United States Patent
Imbach et al.

(10) Patent No.: US 7,795,273 B2
(45) Date of Patent: Sep. 14, 2010

(54) PYRAZOLO[1,5-A]PYRIDINE-3-CARBOXYLIC ACIDS AS EPHB AND VEGFR2 KINASE INHIBITORS

(75) Inventors: Patricia Imbach, Kaiseraugst (CH); Philipp Holzer, Suhr (CH); Pascal Furet, Thann (FR)

(73) Assignee: Novartis AG, Basel (CH)

( * ) Notice: Subject to any disclaimer, the term of this patent is extended or adjusted under 35 U.S.C. 154(b) by 158 days.

(21) Appl. No.: 12/096,260

(22) PCT Filed: Dec. 6, 2006

(86) PCT No.: PCT/EP2006/011722

§ 371 (c)(1),
(2), (4) Date: Jun. 5, 2008

(87) PCT Pub. No.: WO2007/065664

PCT Pub. Date: Jun. 14, 2007

(65) Prior Publication Data

US 2008/0300245 A1    Dec. 4, 2008

(30) Foreign Application Priority Data

Dec. 8, 2005  (GB)  ................. 0525065.9
Jan. 17, 2006 (GB)  ................. 0600931.0

(51) Int. Cl.
 *A01N 43/42*  (2006.01)
 *A61K 31/44*  (2006.01)
 *C07D 491/02* (2006.01)
 *C07D 498/02* (2006.01)

(52) U.S. Cl. ..................... 514/300; 546/121

(58) Field of Classification Search ............... 546/121; 514/300

See application file for complete search history.

(56) References Cited

U.S. PATENT DOCUMENTS

2005/0222171 A1   10/2005   Bold et al.

FOREIGN PATENT DOCUMENTS

WO    2005002552    *    1/2005

OTHER PUBLICATIONS

Anderson et al., Journal of Heterocyclic Chemistry (1981), 18(6), pp. 1149-1152.*
Database Registry, Chemical Abstract Service, Columbus, Ohio, US; 2004, XP002433898, RN 769162-29-0, RN723317-80-4, abstract.

* cited by examiner

*Primary Examiner*—D. Margaret Seaman
*Assistant Examiner*—Niloofar Rahmani

(57) ABSTRACT

The invention relates to novel pyrazolo[1,5-a]pyridine-3-carboxylic acid compounds of the formula

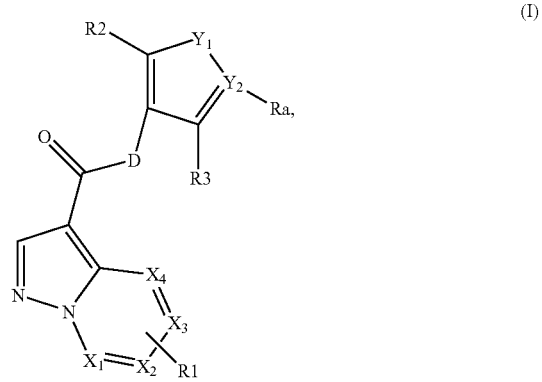

in which all of the variables are as defined in the specification, in free form or in salt form, to their preparation, to their use as medicaments and to medicaments comprising them.

6 Claims, No Drawings

PYRAZOLO[1,5-A]PYRIDINE-3-CARBOXYLIC ACIDS AS EPHB AND VEGFR2 KINASE INHIBITORS

This application is the National Stage of Application No. PCT/EP2006/011722, filed on Dec. 6, 2006, which claims benefit under 35 U.S.C. §119(a)-(d) or 365(b) of United Kingdom (NP) Application No. 0525265.9, filed Dec. 8, 2005, the contents of which are incorporated herein by reference in their entirety.

The invention relates to pyrazolo[1,5-a]pyridine-3-carboxylic acid compounds, their use for the treatment of protein kinase modulation responsive diseases or in the manufacture of pharmaceutical preparations useful in the treatment of said diseases, pharmaceutical preparations, especially useful against said diseases, comprising said compounds and a pharmaceutically acceptable carrier, said compounds for use in the treatment of the animal or human body, especially against said diseases, methods of treatment of the animal or human body comprising administering said compounds to an animal or human, and processes for the manufacture of said compounds, where in each case where compounds are mentioned they can be present as such and/or in the form of (preferably pharmaceutically acceptable) salts.

By the term "protein kinases", a class of enzymatically active proteins is defined where receptor-type kinases and nonreceptor-type kinases can be distinguished, as well as tyrosine and serine/threonine kinases. Regarding their localization, nuclear, cytoplasmic and membrane-associated kinases can be distinguished. Many membrane-associated tyrosine kinases are at the same time receptors for growth factors.

Regarding their catalytic activity, protein kinases (PKs) are enzymes which catalyze the phosphorylation of specific serine, threonine or tyrosine residues in cellular proteins. This post-translational modification of substrate proteins usually works as molecular switch, representing a step in regulating cell proliferation, activation and/or differentiation. Aberrant or excessive or more generally inappropriate PK activity has been observed in several disease states including benign and malignant proliferative disorders. In many cases, it has been possible to treat diseases in vitro and in many cases in vivo, such as proliferative disorders, by making use of PK inhibitors.

Over the past years, basic roles for Eph receptor tyrosine kinases and their ligands, the ephrins, have been understood. Several different Eph receptors are catalogued and grouped into EphA or EphB subclasses, based on their affinity for ligands. At least eight ephrins were identified which are membrane proteins, either of the glycerophosphatidylinositol (GPI)-linked (ephrinA) or transmembrane (ephrinB) type. Signaling between Eph receptors and their ligands appears to be restricted to sites of direct cell-cell contact. The result of contact is the induction of reciprocal bidirectional events between cells. The expression of ephrins and their receptors at certain locations is considered to have impact on tissue patterning and the organizing of spatially very restricted cell loci. Included among the specific effects are the modification of cell migration, adhesion and somite formation.

EphB4 (also named HTK) and its ligand, ephrinB2 (HTKL), play important roles in establishing and determining vascular networks. On the venous epithelium, EphB4 is expressed specifically, while, during early stages of vascular development, ephrinB2 is specifically and reciprocally expressed on arterial endothelial cells. Dysfunctional genes lead to embryonic lethality in mice, and the embryos show identical defects in forming capillary connections in case of either defect ephrinB2 and EphB4. Both are expressed at the first site of hematopoiesis and vascular development during embryogenesis. An essential role for proper hematopoietic, endothelial, hemangioblast and primitive mesoderm development has been established. EphB4 deficiency results in an alteration in the mesodermal differentiation outcome of embryonic stem cells. Ectopic expression of EphB4 in mammary tissue results in disordered architecture, abnormal tissue function and a predisposition to malignancy (see e.g. N. Munarini et al., J. Cell. Sci. 115, 25-37 (2002)). From these and other data, it has been concluded that inadequate EphB4 expression may be involved in the formation of malignancies and thus that inhibition of EphB4 can be expected to be a tool to combat malignancies, e.g. cancer and the like.

The constitutively expressed viral form c-Src (from Rous Sarcoma Virus, a retrovirus) of the tyrosine kinase c-Src found in cells is an example how inadequate expression of the Src protein tyrosine kinase can lead to malignancies based on transformed cells. Inhibition of Src protein tyrosine kinase can lead to inhibition of deregulated growth of the transformed tumor cells, e.g. in connective-tissue tumors. Therefore, also here inhibition of c-Src or modified or mutated forms thereof is expected to show a beneficial effect in the treatment of proliferative diseases.

VEGFRs (vascular endothelial growth factor receptors) are known to be involved in the control of the onset of angiogenesis. As especially solid tumors depend on good blood supply, inhibition of VEGFRs and thus angiogenesis is under clinical investigation in the treatment of such tumors, showing promising results. VEGF is also a major player in leukemias and lymphomas and highly expressed in a variety of solid malignant tumors, correlating well with malignant disease progression. Examples of tumor diseases with VEGFR-2 (KDR) expression are lung carcinomas, breast carcinomas, Non Hodgkin's lymphomas, ovarian carcinoma, pancreatic cancer, malignant pleural mesothelioma and melanoma. In addition to its angiogenic activity, the ligand of VEGFR, VEGF, may promote tumor growth by direct pro-survival effects in tumor cells. Various other diseases are associated with deregulated angiogenesis, e.g. as mentioned below.

The conversion of the abl proto-oncogene into an oncogene has been observed in patients with chronic myelogenous leukemia (CML). A chromosome translocation joins the bcr gene on chromosome 22 to the abl gene from chromosome 9, thereby generating a Philadelphia chromosome. The resulting fusion protein has the amino terminus of the Bcr protein joined to the carboxy terminus of the Abl tyrosine protein kinase. In consequence, the Abl kinase domain becomes inappropriately active, driving excessive proliferation of a clone of hematopoietic cells in the bone marrow. Inhibition of this tyrosine kinase by the active principle of Gleevec™ or Glivec® (trademarks of Novartis), an inhibitor of this fusion protein, has been shown to be a highly active treatment against CML. Thus the general concept that inadequate expression of Abl tyrosine kinase can remedy malignancies, especially leukemias, could be verified.

However, many compounds used as inhibitors of protein kinases so far have can show lack of specificity, undesired side effects that may inter alia be caused by disadvantageous inhibitory properties against more than one type of protein kinases, lack of efficiency due to too high specificity, efficiency only against certain diseases, development of resistance during administration and/or comparable undesirable properties.

This leads to the problem of the present invention: In view inter alia of the large number of protein kinase inhibitors and the multitude of proliferative and other protein kinase-related diseases, as well as in view of the development of resistance against certain therapeutics, there is an ever-existing need to provide new classes of compounds that are useful as protein kinase inhibitors and thus in the treatment of these protein tyrosine kinase, such as serine/threonine and/or preferably PTK (protein tyrosine kinase) related diseases. What is required are new classes of pharmaceutically advantageous protein kinases, especially PTK inhibiting compounds, especially with advantageous properties, such as high affinity and/or selectivity for limited groups of or even singular protein kinases, activity also where resistance against different classes of compounds has been developed, a useful affinity profile against certain groups of kinases or the like. In other terms, there exists a need for novel classes of protein kinase inhibitors that can allow to meet the mentioned or other problems.

Certain 4-substituted hydrazono pyrazolopyrimidines have been described for use as GSK3 kinase inhibitors in the treatment of e.g. diabetes and TIE-2 kinase related diseases, see WO 04/009602, WO 04/009596 or WO 04/009597. On the other hand, certain acyl- or acylamino-substituted arylamino-pyrazolopyrimidines have been described as p38-inhibitors, see WO 03/099280.

GENERAL DESCRIPTION OF THE INVENTION

It has been found now surprisingly that a number of protein kinases which can be involved in signal transmission mediated by trophic factors and in the manifestation of diseases that involve the activity of protein kinases, e.g. in proliferative (e.g. tumor) growth, especially as representative examples for protein tyrosine kinases kinases from the family of the src kinases, especially c-src kinase, VEGF-receptor kinase (e.g. KDR and Flt-1), RET-receptor kinase and/or Ephrin receptor kinases, e.g. EphB2 kinase, EphB4 kinase or related kinases, further abl kinase, especially v-abl or c-abl kinase, b-raf (V599E), EGF receptor kinase or other kinases of the EGF family, for example HER-1 or c-erbB2 kinase (HER-2), Flt-3, lck, fyn, c-erbB3 kinase, c-erbB4 kinase; members of the family of the PDGF-receptor tyrosine protein kinases, for example PDGF-receptor kinase, CSF-1 receptor kinase, Kit-receptor kinase (c-Kit), FGF-receptor kinase, e.g. FGF-R1, FGF-R2, FGF-R3, FGF-R4, c-Raf, casein kinases (CK-1, CK-2, G-CK), Pak, ALK, ZAP70, Jak1, Jak2, Axl, Cdk1, cdk4, cdk5, Met, FAK, Pyk2, Syk, Tie-2, insulin receptor kinase (Ins-R), the receptor kinase of the insulin-like growth factor (IGF-1 kinase), and/or further serine/threonine kinases, for example protein kinase C (PK-C), PK-B, EK-B or cdc kinases, such as CDK1, can be inhibited by a pyrazolo[1,5-a]pyridine-3-carboxylic acid compound according to the invention, as well as (e.g. constitutively activated) mutated forms of any one or more of these (e.g. Bcr-Abl, RET/MEN2A, RET/MEN2B, RET/PTC1-9 or b-raf (V599E)). All these and other protein kinases play a part in growth regulation and transformation in mammalian cells, including human cells. Especially, high efficiency against cellular Eph4B kinase can be found.

In view of these activities, the compounds of the invention can be used for the treatment of protein kinase modulation responsive diseases, such as diseases related to especially aberrant (e.g. unregulated, deregulated or constitutive or the like) or excessive activity of such types of kinases, especially those mentioned and most especially those mentioned as being preferred.

DETAILED DESCRIPTION OF THE INVENTION

The invention, in a first embodiment, relates to a compound of the formula

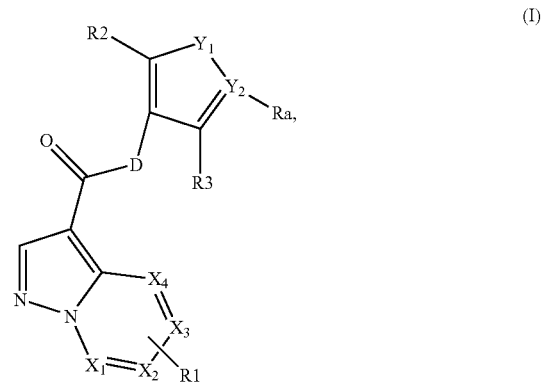

(I)

wherein
R1 is hydrogen, halo, sulfamoyl, N—$C_{1-4}$alkyl sulfamoyl, N,N-di-$C_{1-4}$alkyl sulfamoyl, unsubstituted or substituted alkyl, unsubstituted or substituted aryl, unsubstituted or substituted cycloalkyl or unsubstituted or substituted heterocyclyl;
each of R2 and R3 is, independently of the other, hydrogen, halo, $C_{1-4}$-alkyl, trifluoromethyl, $C_{1-4}$-alkoxy or cyano,
$X_1$, $X_2$, $X_3$ and $X_4$ are CH or up to two of them can be N;
D is N(R6) (preferred), O or S,
  wherein R6 is hydrogen, acyl or unsubstituted or substituted alkyl,
$Y_1$ is O, S, NH, $CH_2$, N=CH, CH=N or CH=CH;
$Y_2$ is C or, if Ra is absent, can be (also) N;
Ra is
  absent if $Y_2$ is N and R1 is unsubstituted alkyl with 5 or more carbon atoms, substituted alkyl, unsubstituted or substituted aryl, unsubstituted or substituted cycloalkyl or unsubstituted or substituted heterocyclyl, or,
  if $Y_2$ is C, is hydrogen if R1 is unsubstituted alkyl with 5 or more carbon atoms, substituted alkyl, unsubstituted or substituted aryl, unsubstituted or substituted cycloalkyl or unsubstituted or substituted heterocyclyl,
  or, if $Y_2$ is C and R1 is hydrogen, halo, $C_{1-4}$-alkyl, sulfamoyl, N—$C_{1-4}$alkyl sulfamoyl, N,N-di-$C_{1-4}$alkyl sulfamoyl, or unsubstituted aryl, is a moiety of the formula IA

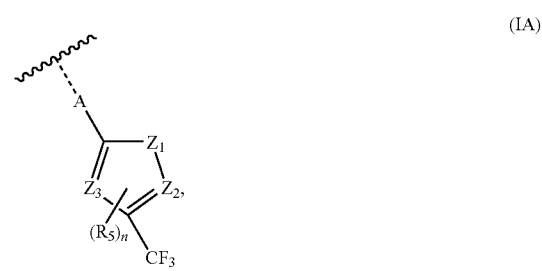

(IA)

wherein the dotted line means the bond binding to the rest of the molecule of the formula I (which is indicated by the wave line),
A is C(=O)—N(R4) or N(R4)-C(=O),
  wherein R4 is hydrogen or unsubstituted or substituted alkyl,
$Z_1$ is O, S, NH, $CH_2$, CH=N, N=CH or CH=CH,
$Z_2$ is nitrogen or CH,
$Z_3$ is CH or N,
each $R_5$ present is, independently of the others, a substituent and
n is 0, 1 or 2, in free form or in salt form.

The invention, in a further embodiment, relates to a compound of the formula I, wherein R1 is hydrogen, halo, sulfamoyl, N—$C_{1-4}$alkyl sulfamoyl, N,N-di-$C_{1-4}$alkyl sulfamoyl, unsubstituted or substituted alkyl, unsubstituted or substituted aryl, or unsubstituted or substituted heterocyclyl;
each of R2 and R3 is, independently of the other, hydrogens or $C_{1-4}$-alkyl,
$X_1, X_2, X_3$ and $X_4$ are CH;
D is N(R6) (preferred), O or S,
  wherein R6 is hydrogen, acyl or unsubstituted or substituted alkyl,
$Y_1$ is O, S, NH, $CH_2$, N=CH, CH=N or CH=CH;
$Y_2$ is C;
Ra is
  hydrogen if R1 is unsubstituted alkyl with 5 or more carbon atoms, substituted alkyl, unsubstituted or substituted aryl, unsubstituted or substituted cycloalkyl or unsubstituted or substituted heterocyclyl,
  or, if R1 is hydrogen, halo, $C_{1-4}$-alkyl, sulfamoyl, N—$C_{1-4}$alkyl sulfamoyl, N,N-di-$C_{1-4}$alkyl sulfamoyl, substituted or unsubstituted aryl, is the moiety of the formula IA,
    A is C(=O)—N(R4) or N(R4)-C(=O),
      wherein R4 is hydrogen or unsubstituted or substituted alkyl,
    $Z_1$ is O, S, NH, $CH_2$, CH=N, N=CH or CH=CH,
    $Z_2$ is nitrogen or CH,
    $Z_3$ is CH or N,
    each $R_5$ present is, independently of the others, a substituent and
    n is 0, 1 or 2, in free form or in salt form.

The invention, in a further embodiment, relates to a compound of the formula I, wherein
R1 is hydrogen, N,N-di-$C_{1-4}$alkyl sulfamoyl, unsubstituted or substituted aryl;
each of R2 and R3 is, independently of the other, hydrogens or $C_{1-4}$-alkyl,
$X_1, X_2, X_3$ and $X_4$ are CH or up to two of them can be N;
D is N(R6) (preferred), O or S,
  wherein R6 is hydrogen, acyl or unsubstituted or substituted alkyl,
$Y_1$ is O, S, NH, $CH_2$, N=CH, CH=N or CH=CH;
$Y_2$ is C;
Ra is
  hydrogen if R1 is unsubstituted alkyl with 5 or more carbon atoms, substituted alkyl, unsubstituted or substituted aryl, unsubstituted or substituted cycloalkyl or unsubstituted or substituted heterocyclyl,
  or, if R1 is hydrogen, N,N-di-$C_{1-4}$alkyl sulfamoyl, or unsubstituted or substituted aryl, is the moiety of the formula IA,
    A is C(=O)—N(R4) or N(R4)-C(=O),
      wherein R4 is hydrogen or unsubstituted or substituted alkyl,
    $Z_1$ is O, S, NH, $CH_2$, CH=N, N=CH or CH=CH,
    $Z_2$ is nitrogen or CH,
    $Z_3$ is CH or N,
    each $R_5$ present is, independently of the others, a substituent and
    n is 0, 1 or 2, in free form or in salt form.

The invention, in a further embodiment, relates to a compound of the formula I, wherein
R1 is hydrogen, N,N-di-$C_{1-4}$alkyl sulfamoyl, unsubstituted or substituted phenyl;
each of R2 and R3 is, independently of the other, hydrogens or $C_{1-4}$-alkyl,
$X_1, X_2, X_3$ and X are CH or up to two of them can be N;
D is N(R6) (preferred), O or S,
  wherein R6 is hydrogen, acyl or unsubstituted or substituted alkyl,
$Y_1$ is O, S, NH, $CH_2$, N=CH, CH=N or CH=CH;
$Y_2$ is C;
Ra is
  hydrogen, if R1 is unsubstituted or substituted phenyl,
  or, if R1 is hydrogen, N,N-di-$C_{1-4}$alkyl sulfamoyl, or unsubstituted phenyl, is the moiety of the formula IA,
    A is C(=O)—N(R4) or N(R4)-C(=O),
      wherein R4 is hydrogen or unsubstituted or substituted alkyl,
    $Z_1$ is O, S, NH, $CH_2$, CH=N, N=CH or CH=CH,
    $Z_2$ is nitrogen or CH,
    $Z_3$ is CH or N,
    each $R_5$ present is, independently of the others, a substituent and
    n is 0, 1 or 2, in free form or in salt form.

The invention, in a further embodiment, relates to a compound of the formula I, wherein
R1 is hydrogen, N,N-di-$C_{1-4}$alkyl sulfamoyl, unsubstituted or substituted phenyl;
each of R2 and R3 is, independently of the other, hydrogen or $C_{1-4}$-alkyl,
$X_1, X_2, X_3$ and $X_4$ are CH;
D is NH,
$Y_1$ is CH=CH;
$Y_2$ is C;
Ra is
  hydrogen, if R1 is substituted phenyl,
  or, if R1 is hydrogen, N,N-di-$C_{1-4}$alkyl sulfamoyl, or unsubstituted phenyl, is the moiety of the formula IA,
    A is C(=O)—N(R4) or N(R4)-C(=O),
      wherein R4 is hydrogen or unsubstituted or substituted alkyl,
    $Z_1$ is O, S, NH, $CH_2$, CH=N, N=CH or CH=CH,
    $Z_2$ is nitrogen or CH,
    $Z_3$ is CH or N,
    each $R_5$ present is, independently of the others, a substituent and
    n is 0, 1 or 2, in free form or in salt form.

The invention, in a further embodiment, relates to a compound of the formula I, wherein
R1 is hydrogen, N,N-di-$C_{1-4}$alkyl sulfamoyl, unsubstituted or substituted phenyl;
each of R2 and R3 is, independently of the other, hydrogen or $C_{1-4}$-alkyl, $X_1$, $X_2$, $X_3$ and $X_4$ are CH;
D is NH,
$Y_1$ is CH=CH;
$Y_2$ is C;
Ra is
   hydrogen, if R1 is substituted phenyl,
   or, if R1 is hydrogen, N,N-di-$C_{1-4}$alkyl sulfamoyl, or unsubstituted phenyl, is the moiety of the formula IA,
      A is C(=O)—NH or NH—C(=O),
      $Z_1$ is CH=CH,
      $Z_2$ is CH,
      $Z_3$ is CH,
      each $R_5$ present is, independently of the others, a substituent and
      n is 0, 1 or 2, in free form or in salt form.

The invention, in a further embodiment, relates to a compound of the formula I, wherein
R1 is hydrogen, or substituted phenyl,
each of R2 and R3 is, independently of the other, hydrogen or $C_{1-4}$-alkyl,
$X_1$, $X_2$, $X_3$ and $X_4$ are CH;
D is NH,
$Y_1$ is CH=CH;
$Y_2$ is C;
Ra is
   hydrogen, if R1 is substituted phenyl,
   or, if R1 is hydrogen, or unsubstituted phenyl, is the moiety of the formula IA,
      A is C(=O)—NH or NH—C(=O),
      $Z_1$ is CH=CH,
      $Z_2$ is CH,
      $Z_3$ is CH,
      each $R_5$ present is, independently of the others, a substituent and
      n is 0, 1 or 2, in free form or in salt form.

The invention relates to the use of a compound of the formula I, or a pharmaceutically acceptable salt thereof, for the treatment of protein kinase modulation responsive diseases, especially in an animal or preferably a human, especially a disease responsive to the inhibition of one or more protein tyrosine kinases (PTKs) mentioned under "General Description of the Invention", more especially one or more PTKs selected from the family of src kinases, especially c-src kinase, VEGF-receptor kinase (e.g. KDR and Flt-1) RET-receptor kinase or Ephrin receptor kinases, e.g. EphB2 kinase, EphB4 kinase or related kinases, or mutated (e.g. constitutively active or otherwise partially or totally deregulated) forms thereof.

The invention also relates to the use of a compound of the formula I, or a (preferably pharmaceutically acceptable) salt thereof, in the manufacture of pharmaceutical preparations useful in the treatment of said diseases, pharmaceutical preparations, especially useful against said diseases, comprising a compound of the formula I, or a pharmaceutically acceptable salt thereof and at least one pharmaceutically acceptable carrier, a compound of the formula I, or a pharmaceutically acceptable salt thereof, for use in the treatment of the animal or human body, especially against a disease mentioned in the preceding paragraph, to a method of treatment of the animal or human body comprising administering a compound of the formula I, or a pharmaceutically acceptable salt thereof, to an animal or human, especially to a patient in need of such treatment in an amount effective for the treatment of said disease, and to a process for the manufacture of a compound of the formula I, or a (prefer-ably pharmaceutically acceptable) salt thereof.

In formula I, the following significances are preferred independently, collectively or in any combination or sub-combination thereof:

The general terms or symbols used hereinbefore and hereinafter preferably have, within the context of this disclosure, the following meanings, unless otherwise indicated:

The term "lower" or "$C_1$-$C_7$-" defines a moiety with up to and including maximally 7, especially up to and including maximally 4, carbon atoms, said moiety being branched (one or more times) or straight-chained. Lower or $C_1$-$C_7$-alkyl, for example, is n-pentyl, n-hexyl or n-heptyl or preferably $C_1$-$C_4$-alkyl, especially as methyl, ethyl, n-propyl, sec-propyl, n-butyl, isobutyl, sec-butyl, tert-butyl. In case of lower alkenyl or lower alkynyl, lower means preferably "$C_2$-$C_7$"-, more preferably "$C_2$-$C_4$-".

Halo or halogen is preferably fluoro, chloro, bromo or iodo, most preferably fluoro, chloro or bromo.

Unsubstituted or substituted alkyl is preferably $C_1$- to $C_{20}$-alkyl, more preferably lower alkyl, e.g. methyl, ethyl or propyl, that can be linear or branched one or more times (provided the number of carbon atoms allows this) and that is unsubstituted or substituted by one or more, preferably up to three, substitutents independently selected from the group consisting of unsubstituted or substituted heterocyclyl as described below, especially pyrrolidino, piperidino, piperidino substituted by amino or N-mono- or N,N-di-[lower alkyl, phenyl and/or phenyl-lower alkyl)-amino, unsubstituted or N-lower alkyl substituted piperidinyl bound via a ring carbon atom, such as 1-isopropyl-piperidin-4-yl, piperazino, lower alkylpiperazino, such as 4-(methyl, ethyl or isopropyl)-piperazino, morpholino or thiomorpholino; unsubstituted or substituted cycloalkyl as described below, unsubstituted or substituted aryl as defined below, especially phenyl or naphthyl; of lower alkenyl, lower alkynyl, halo, hydroxy, lower alkoxy, lower-alkoxy-lower alkoxy, (lower-alkoxy)-lower alkoxy-lower alkoxy, phenoxy, naphthyloxy, phenyl- or naphthyl-lower alkoxy, such as benzyloxy; amino-lower alkoxy, lower-alkanoyloxy, benzoyloxy, naphthoyloxy, nitro, cyano, carboxy, lower alkoxy carbonyl, e.g. methoxy carbonyl, n-propoxy carbonyl, iso-propoxy carbonyl or tert-butoxycarbonyl; phenyl- or naphthyl-lower alkoxycarbonyl, such as benzyloxycarbonyl; lower alkanoyl, such as acetyl, benzoyl, naphthoyl, carbamoyl, N-mono- or N,N-disubstituted carbamoyl, such as N-mono- or N,N-di-substituted carbamoyl wherein the substitutents are selected from lower alkyl and hydroxy-lower alkyl; amidino, guanidino, ureido, mercapto, lower alkylthio, phenyl- or naphthylthio, phenyl- or naphthyl-lower alkylthio, lower alkyl-phenylthio, lower alkyl-naphthylthio, halogen-lower alkylmercapto, lower alkylsulfinyl, phenyl- or naphthyl-sulfinyl, phenyl- or naphthyl-lower alkylsulfinyl, lower alkyl-phenylsulfinyl, lower alkyl-naphthylsulfinyl, sulfo, lower alkanesulfonyl, phenyl- or naphthyl-sulfonyl, phenyl- or naphthyl-lower alkylsulfonyl, lower alkylphenylsulfonyl, halogen-lower alkylsulfonyl, such as trifluoromethanesulfonyl; sulfonamido, benzosulfonamido, amino, N-mono- or N,N-di-[lower alkyl, phenyl and/or phenyl-lower alkyl)-amino, such as N,N-dimethylamino, N,N-diethylamino, 3-[N—(N,N-di-methylamino)-propylamino, 2-[N—(N,N-dimethylamino)-ethylamino or N—(N,N-dimethylamino)-methylamino; where each phenyl or naphthyl (also in phenoxy or naphthoxy) mentioned above as substituent or part of a substituent of substituted alkyl is itself unsubstituted or substituted by one or more, e.g. up to three, preferably 1 or 2, substituents independently selected from halo, especially fluoro, chloro, bromo or iodo, halo-lower alkyl, such as trifluoromethyl, hydroxy, lower alkoxy, amino, N-mono- or N,N-di-(lower alkyl, phenyl, naphthyl, phenyl-lower alkyl and/or naphthyl-lower alkyl)-amino, nitro, carboxy, lower-alkoxycarbonyl carbamoyl, cyano and/or sulfamoyl. Especially preferred as R1 in formula I are lower alkyl, amino-lower alkyl, such as 3-aminopropyl, 2-aminoethyl or 2-aminomethyl, N-mono- or N,N-di-(lower alkyl, phenyl and/or phenyl-lower alkyl)-amino-lower alkyl, such as 3-(N,N-dimethyl-amino)-propyl, 3-(N,N-diethylamino)-propyl, 2-(N,N-dimethylamino)-ethyl, 2-(N,N-diethyl-amino)-ethyl, N,N-dimethylaminomethyl or N,N-diethylaminomethyl, pyrrolidino-lower alkyl, piperidino-lower alkyl, 1-lower allylpiperidin-4-yl-lower alkyl, 4-[N-mono- or N,N-di-(lower alkyl, phenyl and/or phenyl-lower alkyl)-amino]-piperidino, piperazino-lower alkyl, such as piperazino-methyl, 4-lower alkylpiperazino-lower alkyl, such as 4-(methyl, ethyl or isopropyl)-piperazino-methyl, or (morpholino or thiomorpholino)-lower alkyl. Alkyl with 5 or more carbon atoms is especially $C_5$-$C_{20}$-alkyl. Preferably, as then especially binding to the active enzyme conformation is found, R1 is $C_5$-$C_{20}$-alkyl or substituted $C_1$-$C_{20}$-alkyl while then Ra in formula I is absent or (if $Y_2$ is C) hydrogen. Alternatively, as then especially binding to the inactive enzyme conformation is found, preferably $R_1$ is $C_1$-$C_4$-alkyl or especially hydrogen while then $Y_2$ is C and Ra in formula I is a moiety of the formula IA shown above.

Unsubstituted or substituted aryl is preferably an unsaturated carbocyclic system of not more than 20 carbon atoms, especially not more than 16 carbon atoms, is preferably mono-, bi- or tri-cyclic, which is unsubstituted or, in the case of substituted aryl, substituted preferably by one or more, preferably up to three, e.g. one or two substituents independently selected from the group consisting of phenyl, naphthyl, phenyl- or naphthyl-lower alkyl, such as benzyl; hydroxy-lower alkyl, such as hydroxymethyl; lower-alkoxy-lower alkyl, (lower-alkoxy)-lower alkoxy-lower alkyl, lower alkanoyl-lower alkyl, halo-lower alkyl, such as trifluoromethyl; phenoxy- or naphtyloxy-lower alkyl, phenyl- or naphthyl-lower alkoxy-lower alkyl, such as benzyloxy-lower alkyl; lower alkoxy-carbonyloxy-lower alkyl, such as tert-butoxycarbonyloxy-lower alkyl; phenyl- or naphthyl-lower alkoxycarbonyloxy-lower alkyl, such as benzyloxy-carbonyloxy-lower alkyl; cyano-lower alkyl, lower alkenyl, lower alkynyl, lower alkanoyl, such as acetyl; halo, hydroxy, lower alkoxy, such as methoxy, lower-alkoxy-lower alkoxy, (lower-alkoxy)-lower alkoxy-lower alkoxy, phenoxy, naphthyloxy, phenyl- or naphthyl-lower alkoxy, such as benzyloxy; amino-lower alkyl, lower-alkanoyloxy, benzoyloxy, naphthoyloxy, nitro, amino, mono-, di- or tri-substituted (in the latter case quaternary and positively charged) amino wherein the amino substituents are independently selected from lower alkyl, lower alkanoyl, lower alkanesulfonyl, such as methanesulfonyl, phenyl, naphthyl, phenyl-lower alkyl and naphthyl-lower alkyl; cyano, carboxy, lower alkoxy carbonyl, e.g. methoxy carbonyl, n-propoxy carbonyl, iso-propoxy carbonyl or tert-butoxycarbonyl; phenyl- or naphthyl-lower alkoxycarbonyl, such as benzyloxycarbonyl; benzoyl, naphthoyl, carbamoyl, N-mono- or N,N-disubstituted carbamoyl, such as N-mono- or N,N-di-substituted carbamoyl wherein the substitutents are selected from lower alkyl and hydroxy-lower alkyl; amidino, guanidino, ureido, mercapto, lower alkylthio, phenyl- or naphthylthio, phenyl- or naphthyl-lower alkylthio, lower alkyl-phenylthio, lower alkyl-naphthylthio, halogen-lower alkylmercapto, lower alkylsulfinyl, phenyl- or naphthyl-sulfinyl, phenyl- or naphthyl-lower alkylsulfinyl, lower alkyl-phenylsulfinyl, lower alkyl-napthylsulfinyl, sulfo, lower alkanesulfonyl, phenyl- or naphthyl-sulfonyl, phenyl- or naphthyl-lower alkylsulfonyl, lower alkylphenylsulfonyl, halogen-lower alkylsulfonyl, such as trifluoromethanesulfonyl; sulfonamido, benzosulfonamido, pyrrolidino, piperidino, piperidino substituted by amino or N-mono- or N,N-di-[lower alkyl, phenyl and/or phenyl-lower alkyl)-amino, unsubstituted or N-lower alkyl substituted piperidinyl bound via a ring carbon atom, such as 1-isopropyl-piperidin-4-yl, piperazino, lower alkylpiperazino, such as 4-(methyl, ethyl or isopropyl)-piperazino, morpholino or thiomorpholino; where each phenyl or naphthyl (also in phenoxy or naphthoxy) mentioned above as substitutent or part of a substituent of substituted aryl is itself unsubstituted or substituted by one or more, e.g. up to three, preferably 1 or 2, substituents independently selected from halo, especially fluoro, chloro, bromo or iodo, halo-lower alkyl, such as trifluoromethyl, hydroxy, lower alkoxy, amino, N-mono- or N,N-di-(lower alkyl, phenyl, naphthyl, phenyl-lower alkyl and/or naphthyl-lower alkyl)amino, nitro, carboxy, lower-alkoxycarbonyl carbamoyl, cyano and/or sulfamoyl. Unsubstituted or substituted aryl, especially as R1 in formula I, is preferably phenyl that is unsubstituted or substituted by halo, more preferably by lower alkoxy, nitro, amino, lower alkanoyl-amino, N-lower alkanesulfonylamino, such as methanesulfonyl amino, N-mono-, N,N-di- or N,N,N-tri-(lower alkyl, phenyl and/or phenyl-lower alkyl)-amino (the latter corresponding to a quaternary amino=quaternary ammonio), pyrrolidino, piperidino, piperidino substituted by amino or N-mono- or N,N-di-[lower alkyl, phenyl and/or phenyl-lower alkyl)-amino, unsubstituted or N-lower alkyl substituted piperidinyl bound via a ring carbon atom, such as 1-iso-propyl-piperidin-4-yl, piperazino, lower alkylpiperazino, such as 4-(methyl, ethyl or isopropyl)-piperazino, $C_{1-7}$alkoxy-carbonyl-piperazino, e.g. tert-butyloxycarbonyl-piperazino, cycloalkoxy-carbonyl-piperazino, aryloxycarbonyl-piperazino, morpholino or thiomorpholino. Preferably, the aryl is phenyl.

Preferably, the substituted aryl, e.g. substituted phenyl, is substituted by one or 2 of the following substituents: $C_{1-7}$-alkoxy, e.g. $C_{1-4}$-alkoxy, morpholino, N,N-di-$C_{1-7}$-alkylamino, e.g. N,N-di-$C_{1-4}$-alkylamino, $C_{1-7}$alkoxy-carbonyl-piperazino, e.g. tert-butyloxycarbonyl-piperazino, cycloalkoxy-carbonyl-piperazino, aryloxycarbonyl-piperazino.

In unsubstituted or substituted cycloalkyl, cycloalkyl is preferably a saturated mono- or bicyclic hydrocarbon group with 3 to 16, more preferably 3 to 9 ring carbon atoms, e.g. cyclopropyl, cyclobutyl, cyclopentyl, cyclohexyl, cycloheptyl or cyclooctyl, and is substituted by one or more, preferably one to three, substitutents independently selected from those described for substituted aryl or is (preferably) unsubstituted.

Unsubstituted or substituted heterocyclyl is preferably a heterocyclic radical that is unsaturated, saturated or partially saturated and is preferably a monocyclic or in a broader aspect of the invention bicyclic or tricyclic ring; and has 3 to 24, more preferably 4 to 16, most preferably 4 to 10 ring atoms; wherein one or more, preferably one to four, especially one or two carbon ring atoms are replaced by a heteroatom selected from the group consisting of nitrogen, oxygen and sulfur, the bonding ring preferably having 4 to 12, especially 5 to 7 ring atoms; which heterocyclic radical (heterocyclyl) is unsubstituted or substituted by one or more, especially 1 to 3, substituents independently selected from the group consisting of the substituents defined above under "substituted aryl"; and where heterocyclyl is especially a heterocyclyl radical selected from the group consisting of oxiranyl, azirinyl, aziridinyl, 1,2-oxathiolanyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, (S-oxo or S,S-dioxo)-thiomorpholinyl, indolizinyl, isoindolyl, 3H-indolyl, indolyl, benzimidazolyl, cumaryl, indazolyl, triazolyl, tetrazolyl, purinyl, 4H-quinolizinyl, iso-quinolyl, quinolyl, tetrahydroquinolyl, tetrahydroisoquinolyl, decahydroquinolyl, octahydro-isoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, beta-carbolinyl, phenanthridinyl, acridinyl, perimidinyl, phenanthrolinyl, furazanyl, phenazinyl, phenothiazinyl, phenoxazinyl, chromenyl, isochromanyl and chromanyl, each of these radicals being unsubstituted or substituted by one to two radicals selected from the group consisting of lower alkyl, especially methyl or tert-butyl, lower alkoxy, especially methoxy, and halo, especially bromo or chloro.

$X_1$, $X_2$, $X_3$ and $X_4$ are preferably all CH.

Acyl is preferably an organic moiety selected from unsubstituted or substituted alkyl, unsubstituted or substituted aryl, unsubstituted or substituted heterocyclyl or unsubstituted or substituted cycloalkyl, each preferably as described above, bound via a carbonyl (—C(=O)—) or sulfonyl (—S(=O)$_2$—) group to the rest of the molecule of the formula I, that is, a moiety derived from an organic carboxylic or sulfonic acid. Preferred are alkanoyl, especially lower alkanoyl, e.g. acetyl, propionyl or butyroyl, benzoyl (=phenylcarbonyl), naphthoyl (=naphthylcarbonyl), phenyl-$C_1$-$C_7$alkylcarbonyl, naphthyl-$C_1$-$C_7$-alkylcarbonyl, phenylsulfonyl or lower alkanesulfonyl, where each lower alkanoyl as acyl or each phenyl or naphthyl mentioned as part of acyl are unsubstituted or substituted by one or more, e.g. up to three, preferably 1 or 2, substituents independently selected from halo, especially fluoro, chloro, bromo or iodo, halo-lower alkyl, such as trifluoromethyl, hydroxy, lower alkoxy, amino, N-mono- or N,N-di-(lower alkyl, phenyl, naphthyl, phenyl-lower alkyl or naphthyl-lower alkyl)amino, nitro, carboxy, lower-alkoxycarbonyl, carbamoyl, cyano and/or sulfamoyl. Preferred are lower alkanoyl, benzoyl, phenylsulfonyl or toluolsulfonyl.

$Y_1$ is preferably N=CH, CH=N or most preferably CH=CH.

$Y_2$ is C (carbon) or (if Ra is absent) can be N, meaning that $Y_2$—Ra can be C(Ra) or N, preferably, $Y_2$ is C.

In a moiety of the formula IA as shown above, "the dotted line means the bond binding to the rest of the molecule of the formula I (which is indicated by the wave line)" means that the dotted line corresponds to the bond binding Ra in formula I.

Unsubstituted or substituted alkyl R4 can be unsubstituted or substituted alkyl as defined above; preferred is lower alkyl or phenyl-lower alkyl.

$Z_1$ is preferably CH=N or N=CH or more preferably CH=CH (thus forming a six-membered ring).

Each of $Z_2$ and $Z_3$ is preferably CH.

The substitutents R5 (if present, that is, if n is 1 or 2) are preferably independently selected from the substituents mentioned above for substituted aryl; especially selected from the group consisting of lower alkyl, halo, halo-lower alkyl, such as trifluoromethyl lower alkanoyl, such as acetyl; hydroxy, lower alkoxy, such as methoxy, nitro, amino, mono- or di-substituted amino wherein the amino substituents are independently selected from lower alkyl and lower alkanoyl, cyano, carboxy, lower alkoxy carbonyl, e.g. methoxy carbonyl, carbamoyl, N-mono- or N,N-di-(lower alkyl)-substituted carbamoyl, amidino, guanidino, ureido, lower alkylthio, sulfo, lower alkanesulfonyl and sulfonamido. R5 is preferably $C_{1-7}$alkoxy, even preferably $C_{1-4}$-alkoxy.

The symbol n preferably stands for 0 or 1.

Salts are especially the pharmaceutically acceptable salts of compounds of formula I. They can be formed where salt forming groups, such as basic or acidic groups, are present that can exist in dissociated form at least partially, e.g. in a pH range from 4 to 10 in aqueous environment, or can be isolated especially in solid form, or where charged groups (e.g. quaternary ammonium) are present—in the latter case acylate salts are formed with anions of organic or inorganic acids (e.g. as defined in the next paragraph).

Such salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethane-sulfonic acid, ethane-1,2-disulfonic acid, benzenesulfonic acid, 2-naphthalenesulfonic acid, 1,5-naphthalene-disulfonic acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethyl-amine or tri(2-hydroxyethyl)amine, or heterocyclic bases, for example N-ethyl-piperidine or N,N'-dimethylpiperazine.

When a basic group and an acid group are present in the same molecule, a compound of formula I may also form internal salts.

For isolation or purification purposes it is also possible to use pharmaceutically unacceptable salts, for example picrates or perchlorates. For therapeutic use, only pharmaceutically acceptable salts or free compounds are employed (where applicable comprised in pharmaceutical preparations), and these are therefore preferred.

In view of the close relationship between compounds in free form and in the form of their salts, including those salts that can be used as intermediates, for example in the purification or identification of the compounds or salts thereof, any reference to "compounds" or "a compound" (including also starting materials and "intermediates") hereinbefore and hereinafter, especially to the compound(s) of the formula I, is to be understood as referring also to one or more salts thereof or a mixture of a free compound and one or more salts thereof, each of which is intended to include also any solvate, metabolic precursor such as ester or amide of the compound of formula I, or salt of any one or more of these, as appropriate and expedient and if not explicitly mentioned otherwise. Different crystal forms and solvates may be obtainable and then are also included.

Where the plural form is used for compounds, salts, pharmaceutical preparations, diseases, disorders and the like, this is intended to mean to include also a single compound, salt, pharmaceutical preparation, disease or the like, where "a" or "an" is used, this means to refer to the indefinite article or preferably to "one".

In some cases, a compound of the present invention may comprise one or more chiral centers in substituents or show other asymmetry (leading to enantiomers) or may otherwise be able to exist in the form of more than one stereoisomer, e.g. due more than one chiral centers or more than one other type of asymmetry or due to rings or double bonds that allow for Z/E (or cis-trans) isomerism (diastereomers). The present inventions includes both mixtures of two or more such isomers, such as mixtures of enantiomers, especially racemates, as well as preferably purified isomers, especially purified enantiomers or enantiomerically enriched mixtures.

The compounds of formula I have valuable pharmacological properties and are useful in the treatment of protein kinase, especially protein tyrosine kinase (especially one or more of the protein kinases mentioned above under 'General Description of the invention', most especially c-src kinase, VEGF-receptor kinase (e.g. KDR and Flt-1), RET-receptor kinase and/or Ephrin receptor kinases, e.g. EphB2 kinase, EphB4 kinase or related kinases) modulation responsive diseases, where modulation preferably means inhibition and responsive means that the progress of a disease and/or its symptoms is slowed, stopped or even inverted up to and including a complete or at least temporary cure. The term "treatment" includes especially prophylaxis including preventative treatment, e.g. in patients where mutations or changes have been found that indicate that they are or may be prone to the development of a disease, or preferably therapeutic (including but not limited to palliative, curative, symptom-alleviating, symptom-reducing, disease- or symptom-suppressing, progression-delaying, kinase-regulating and/or kinase-inhibiting) treatment of said diseases, especially of any one or more of the diseases mentioned below.

The term "curative" as used herein preferably means efficacy in treating ongoing episodes involving (specially deregulated) receptor tyrosine kinase activity. The term "prophylactic" preferably means the prevention of the onset or recurrence of diseases involving deregulated receptor tyrosine kinase activity.

The term "delay of progression" as used herein especially means administration of the active compound to patients being in a pre-stage or in an early phase of the disease to be treated, in which patients for example a pre-form of the corresponding disease is diagnosed or which patients are in a condition, e.g. during a medical treatment or a condition resulting from an accident, under which it is likely that a corresponding disease will develop, or where e.g. metastasation can be expected without treatment.

An animal is preferably a warm-blooded animal, more preferably a mammal. A human (which generally also falls under the general term "animal") is especially a patient or a person that (e.g. due to some mutation or other features) is prone to a risk for a disease as defined above or below.

Where subsequently or above the term "use" is mentioned (as verb or noun) (relating to the use of a compound of the formula I or a pharmaceutically acceptable salt thereof), this (if not indicated differently or suggested differently by the context) includes any one or more of the following embodiments of the invention, respectively (if not stated otherwise): the use in the treatment of a protein (especially tyrosine) kinase modulation (especially inhibition) responsive disease, the use for the manufacture of pharmaceutical compositions for use in the treatment of a protein kinase modulation (especially inhibition) responsive disease, methods of use of one or more compounds of the formula I in the treatment of a protein kinase modulation (especially inhibition) responsive and/or proliferative disease, pharmaceutical preparations comprising one or more compounds of the formula I for the treatment of said protein kinase modulation (especially inhibition) responsive disease, and one or more compounds of the formula I in the treatment of said protein kinase modulation (especially inhibition) responsive disease, as appropriate and expedient, if not stated otherwise. In particular, diseases to be treated and are thus preferred for "use" of a compound of formula I are selected from (especially tyrosine) protein kinase modulation (especially inhibition) responsive (meaning also "supported", not only "dependent", including also situations where a disease is responding to modulation, especially inhibition, of a protein kinase, that is, the activity of the protein kinase supports or even causes disease manifestation) diseases mentioned below, especially proliferative diseases mentioned below.

Where a protein kinase is mentioned, this relates to any type of protein kinase, especially one of those defined above under "General Description of the Invention", more especially serine/threonine and/or preferably protein tyrosine kinases, most preferably one or more tyro-sine protein kinases, especially selected from the group consisting of c-src kinase, VEGF-receptor kinase (e.g. KDR and Flt-1), RET-receptor kinase and/or Ephrin receptor kinases, e.g. EphB2 kinase, EphB4 kinase or related kinases, including one or more altered or mutated or allelic forms of any one or more of these (e.g. those that result in conversion of the respective proto-oncogene into an oncogene, such as constitutively activated mutants, e.g. Bcr-Abl). Especially an abnormally highly-expressed, constitutively activated or normal but in the given context of other regulatory mechanism in a patient relatively overactive, and/or mutated form is encompassed.

The usefulness of the compounds of the present invention in the modulation, especially as inhibitors, of protein kinases can especially and paradigmatically be demonstrated by the following test systems for the protein kinases mentioned as preferred above:

In the following description of typical exemplary testing systems, the following abbreviations have the following meanings: DMSO=dimethyl sulfoxide; DTT=dithiothreitol; EDTA=ethylene diamine tetraacetate; MOI=multiplicity of infection; PMSF=p-toluenesulfonyl fluoride; Tris=tris(hydroxymethyl)aminomethane. An "inhibitor" is a test compound of the formula I if not mentioned otherwise.

The efficacy of compounds of the formula I as inhibitors or Ephrin B4 receptor (EphB4) kinases can be demonstrated as follows:

Generation of Bac-to-Bac™ (Invitrogen Life Technologies, Basel, Switzerland) GST-fusion expression vectors: Entire cytoplasmatic coding regions of the EphB-class are amplified by PCR from cDNA libraries derived from human placenta or brain, respectively. Recombinant baculovirus are generated that express the amino acid region 566-987 of the human EphB4 receptor (SwissProt Database, Accession No. P54760). GST sequence is cloned into pFastBac1® vector (Invitrogen Life Technologies, Basel, Switzerland) and PCR amplified. cDNAs encoding EphB4-receptor domains, respectively are cloned in frame 3'prime to the GST sequence into this modified FastBac1 vector to generate pBac-to-Bac™ donor vectors. Single colonies arising from the transformation are inoculated to give overnight cultures for small scale plasmid preparation. Restriction enzyme analysis of plasmid DNA reveals several clones to contain inserts of the expected size. By automated sequencing the inserts and approximately 50 bp of the flanking vector sequences are confirmed on both strands.

Production of viruses: Viruses for each of the kinases are made according to the protocol supplied by GIBCO if not stated otherwise. In brief, transfer vectors containing the kinase domains are transfected into the DH10Bac cell line (GIBCO) and plated on selective agar plates. Colonies without insertion of the fusion sequence into the viral genome (carried by the bacteria) are blue. Single white colonies are picked and viral DNA (bacmid) isolated from the bacteria by standard plasmid purification procedures. Sf9 cells or Sf21 cells are then transfected in 25 cm$^2$ flasks with the viral DNA using Cellfectin reagent according to the protocol.

Purification of GST-tagged kinases: The centrifuged cell lysate is loaded onto a 2 mL glutathione-sepharose column (Pharmacia) and washed three times with 10 mL of 25 mM Tris-HCl, pH 7.5, 2 mM EDTA, 1 mM DTT, 200 mM NaCl. The GST-tagged proteins are then eluted by 10 applications (1 mL each) of 25 mM Tris-HCl, pH 7.5, 10 mM reduced-glutathione, 100 mM NaCl, 1 mM DTT, 10% Glycerol and stored at −70° C.

Protein kinase assays: The activities of protein kinases are assayed in the presence or absence of inhibitors, by measuring the incorporation of $^{33}$P from [γ$^{33}$P]ATP into a polymer of glutamic acid and tyrosine (poly(Glu,Tyr)) as a substrate. The kinase assays with purified GST-EphB (30 ng) are carried out for 15-30 min at ambient temperature in a final volume of 30 μL containing 20 mM Tris.HCl, pH 7.5, 10 mM MgCl$_2$, 3-50 mM MnCl$_2$, 0.01 mM Na$_3$VO$_4$, 1% DMSO, 1 mM DTT, 3 μg/mL poly(Glu,Tyr) 4:1 (Sigma; St. Louis, Mo., USA) and 2.0-3.0 μM ATP (γ-[$^{33}$P]-ATP 0.1 μCi). The assay is terminated by the addition of 20 μL of 125 mM EDTA. Subsequently, 40 μl of the reaction mixture are transferred onto Immobilon-PVDF membrane (Millipore, Bedford, Mass., USA) previously soaked for 5 min with methanol, rinsed with water, then soaked for 5 min with 0.5% H$_3$PO$_4$ and mounted on vacuum manifold with disconnected vacuum source. After spotting all samples, vacuum is connected and each well rinsed with 200 μl 0.5% H$_3$PO$_4$. Membranes are removed and washed 4× on a shaker with 1.0% H$_3$PO$_4$, once with ethanol. Membranes are counted after drying at ambient temperature, mounting in Packard TopCount96-well frame, and addition of 10 μL/well of Microscin™ (Packard). IC$_{50}$ values are calculated by linear regression analysis of the percentage inhibition of each compound in duplicate, at four concentrations (usually 0.01, 0.1, 1 and 10 μM). One unit of protein kinase activity is defined as 1 nmole of $^{33}$P ATP transferred from [γ$^{33}$P] ATP to the substrate protein per minute per mg of protein at 37° C. Compounds of formula I show EphB4 inhibition down to 1 nM, preferably IC$_{50}$ values between 0.001-10 μM.

Alternatively, EphB4 receptor autophosphorylation can be measured as follows:

The inhibition of EphB4 receptor autophosphorylation can be confirmed with an in vitro experiment in cells such as transfected A375 human melanoma cells (ATCC Number: CRL-1619), which permanently express human EphB4 (SwissProt AccNo P54760), are seeded in complete culture medium (with 10% fetal calf serum=FCS) in 6-well cell-culture plates and incubated at 37° C. under 5% CO2 until they show about 90% confluency. The compounds to be tested are then diluted in culture medium (without FCS, with 0.1% bovine serum albumin) and added to the cells. (Controls comprise medium without test compounds). Ligand induced autophosphorylation is induced by the addition of 1 microg/ml soluble ephrinB2-Fc (s-eph-rinB2-Fc: R&D Biosystems, CatNr 496-EB) and 0.1 microM ortho-vanadate. After a further 20 minutes incubation at 37° C., the cells are washed twice with ice-cold PBS (phosphate-buffered saline) and immediately lysed in 200 μl lysis buffer per well. The lysates are then centrifuged to remove the cell nuclei, and the protein concentrations of the supernatants are determined using a commercial protein assay (PIERCE). The lysates can then either be immediately used or, if necessary, stored at −20° C.

A sandwich ELISA is carried out to measure the EphB4 phosphorylation: To capture phosphorylated EphB4 protein 100 ng/well of ephrinB2-Fc (s-ephrinB2-Fc: R&D Biosystems, CatNr 496-EB) is immobilized MaxiSorb (Nunc) ELISA plates. The plates are then washed and the remaining free protein-binding sites are saturated with 3% TopBlock® (Juro, Cat. # TB232010) in phosphate buffered saline with Tween 20® (polyoxyethylen (20)sorbitane monolaurate, ICI/Uniquema) (PBST). The cell lysates (100 μg protein per well) are then incubated in these plates for 1 h at room temperature. After washing the wells three times with PBS an antiphosphotyrosine antibody coupled with alkaline phosphatase (PY 20 Alkaline Phosphate conjugated: ZYMED, Cat Nr03-7722) is added and incubated for another hour. The plates are washed again and the binding of the antiphosphotyrosine antibody to the captured phosphorylated receptor is then demonstrated and quantified using 10 mM D-nitrophenylphosphate as substrate and measuring the OD at 405 nm after 0.5 h-1 h.

The difference between the signal of the positive control (stimulated with vanadate and s-ephrinB2-Fc) and that of the negative control (not stimulated) corresponds to maximal EphB4 phosphorylation (=100%). The activity of the tested substances is calculated as percent inhibition of maximal EphB4 phosphorylation, wherein the concentration of substance that induces half the maximum inhibition is defined as the IC$_{50}$ (inhibitory dose for 50% inhibition). With compounds of the formula I, IC$_{50}$ values between 0.0005 and 20 μM, preferably 0.0005 and 10 μM can be found.

The compounds of formula I can also inhibit other tyrosine protein kinases such as especially the c-Src kinase which plays a part in growth regulation and transformation in animals, especially mammal cells, including human cells. An appropriate assay is described in Andre-jauskas-Buchdunger et al., Cancer Res. 52, 5353-8 (1992). Using this test system, compounds of the formula I can show IC$_{50}$ values for inhibition of c-Src in the range of e.g. 0.001 to 20 μM, usually between 0.005 and 10 μM.

The activity of the compounds of the invention as inhibitors of KDR protein-tyrosine kinase activity can be demonstrated as follows: The inhibition of VEGF-induced receptor autophosphorylation can be confirmed in cells such as transfected CHO cells, which permanently express human VEGF-R2 receptor (KDR), and are seeded in complete culture medium (with 10% fetal calf serum=FCS) in 6-well cell-culture plates and incubated at 37° C. under 5% CO$_2$ until they show about 80% confluency. The compounds to be tested are then diluted in culture medium (without FCS, with 0.1% bovine serum albumin) and added to the cells. Controls comprise medium without test compounds. After 2 h incubation at 37° C., recombinant VEGF is added; the final VEGF concentration is 20 ng/ml. After a further incubation period of five minutes at 37° C., the cells are washed twice with ice-cold PBS (phosphate-buffered saline) and immediately lysed in 100 μl lysis buffer per well. The lysates are then centrifuged to remove the cell nuclei, and the protein concentrations of the supernatants are determined using a commercial protein assay (BIORAD). The lysates can then either be immediately used or, if necessary, stored at −20° C. Using this protocol, selective compounds of the formula I can be found to show IC$_{50}$ values for KDR inhibition that are preferably at least 1.5 times higher than for c-Abl tyrosine kinase, more preferably more than 2 times higher than for EphB4 tyrosine kinase. Generally, in this test system with compounds of the formula I $IC_{50}$ values are found in the range from 0.001 to 20 µM, more preferably from 0.005 to 10 µM.

Compounds of the formula I can also inhibit other protein kinases.

The efficacy of the compounds of the invention as inhibitors of c-Abl protein-tyrosine kinase activity can be demonstrated as follows:

An in vitro enzyme assay is performed in 96-well plates as a filter binding assay as described by Geissler et al. in Cancer Res. 1992; 52:4492-4498, with the following modifications. The His-tagged kinase domain of c-Abl is cloned and expressed in the baculovirus/Sf9 system as described by Bhat et al. in J. Biol. Chem. 1997; 272:16170-16175. A protein of 37 kD (c-Abl kinase) is purified by a two-step procedure over a Cobalt metal chelate column followed by an anion exchange column with a yield of 1-2 mg/L of Sf9 cells (Bhat et al., reference cited). The purity of the c-Abl kinase is >90% as judged by SDS-PAGE after Coomassie blue staining. The assay contains (total volume of 30 µL): c-Abl kinase (50 ng), 20 mM Tris.HCl, pH 7.5, 10 mM $MgCl_2$, 10 µM $Na_3VO_4$, 1 mM DTT and 0.06 µCi/assay [$\gamma^{33}$ P]-ATP (5 µM ATP) using 30 µg/mL poly-Ala,Glu,Lys,Tyr-6:2:5:1 (Poly-AEKY, Sigma P1152) in the presence of 1% DMSO. Reactions are terminated by adding 10 µL of 250 mM EDTA and 30 µL of the re-action mixture is transferred onto Immobilon-PVDF membrane (Millipore, Bedford, Mass., USA) previously soaked for 5 min with methanol, rinsed with water, then soaked for 5 min with 0.5% $H_3PO_4$ and mounted on vacuum manifold with disconnected vacuum source. After spotting all samples, vacuum is connected and each well rinsed with 200 µL 0.5% $H_3PO_4$. Membranes are removed and washed on a shaker with 0.5% $H_3PO_4$ (4 times) and once with ethanol. Membranes are counted after drying at ambient temperature, mounting in Packard TopCount 96-well frame, and addition of 10 µL/well of Microscint™ (Packard). Using this test system, compounds of the formula I can show $IC_{50}$ values of inhibition for c-Abl inhibition in the range of e.g. 0.002 to 100 µM, usually between 0.002 and 5 µM.

Further, compounds of the formula I can also be used to inhibit b-raf (V599E). The activity of B-Raf-V599E is assayed in the presence or absence of inhibitors measuring the incorporation of $^{33}P$ from [$\gamma^{33}P$]ATP into (His)-IκB. The test compound is dissolved in DMSO (10 mM) and stored at −20° C. Serial dilutions are made in DMSO freshly and further diluted with pure water to obtain 3 times concentrated test solutions in 3% DMSO. The final volume (30 µl) of the assay contains 10 µl of test solution (1% DMSO), 10 µl assay mix (20 mM Tris-HCl, pH 7.5, 3 mM $MnCl_2$, 3 mM $MgCl_2$, 1 nM DTT, 3 µg/ml (His)-IκB. 1% DMSO and 3.5 µM ATP [$\gamma^{33}P$]-ATP 0.1 µCi) and 10 µl enzyme dilution (600 ng of GST-B-Raf-V599E). The pipetting steps are programmed to be performed either on the MultiPROBE IIx, MultiPROBE IIIx or HamiltonSTAR robots in the 96-well format. The assay is carried out as described in the literature (see C. Garcia-Echeverria et al., Cancer Cell. 5, 231-9 (2004)) terminated by the addition of 20 µl 125 mM EDTA. The capturing of the phosphorylated peptides by the filter binding method is performed as following: 40 µl of the reaction mixture are transferred onto Immobilon-PVDF membranes previously soaked for 5 min with methanol, rinsed with water, then soaked for 5 min with 0.5% $H_3PO_4$ and mounted on vacuum manifold with disconnected vacuum source. After spotting all samples, vacuum is connected and each well rinsed with 200 µl 0.5% $H_3PO_4$. Free membranes are removed and washed 4× on a shaker with 1.0% $H_3PO_4$, once with ethanol. Membranes are counted after drying at ambient temperature, mounting in Packard TopCount 96 well frame and addition of 10 µl/well of Microscint™. The plates are eventually sealed and counted in a microplate scintillation counter (TopCount NXT, TopCount NXT HTS). In case of the flash plate method, the kinase reaction is first carried out in polystyrene-based plastic plates and then stopped after 60 min by the addition of 20 µl of 125 mM EDTA. For capturing (60 min, RT), the biotinylated substrate is transfer-red to Nickel-coated flash plates. The assay plates are washed three times with PBS and dried at room temperature. Afterwards, the plates are sealed and counted in a microplate scintillation counter (TopCount NXT, TopCount NXT HTS). $IC_{50}$ values are calculated by linear regression analysis of percentage inhibition by the compound either in duplicate, at four concentrations (usually 0.01, 0.1, 1 and 10 µM) or as 8 single point $IC_{50}$ starting at 10 µM followed by 1:3 dilutions. For b-raf inhibition, compounds of the formula I can show $IC_{50}$ values in the range from 0.05 to 50 µM.

The results indicate an advantageous affinity profile of the compounds of the formula I.

There are also experiments to demonstrate the antitumor activity of compounds of the formula I in vivo. For example, in order to test whether a compound of the formula I inhibits angiogenesis in vivo, its effect on the angiogenic response induced by an angiogenenic factor such as VEGF, bFGF, S-1P. PDGF or IGF-1 in a growth factor implant model in mice is tested: A porous Teflon chamber (volume 0.5 mL) is filled with 0.8% w/v agar containing heparin (20 units/ml) with or without growth factor (2 µg/ml human VEGF) is implanted subcutaneously on the dorsal flank of C57/C6 mice. The mice are treated with the test compound (e.g. 5, 10, 25, 50 or 100 mg/kg p.o. once daily) or vehicle starting on the day of implantation of the chamber and continuing for 4 days after. At the end of the treatment, the mice are killed, and the chambers are removed. The vascularrized tissue growing around the chamber is carefully removed and weighed, and the blood content is assessed by measuring the hemoglobin content of the tissue (Drabkins method; Sigma, Deisenhofen, Germany). Tie-2 protein levels, as a measure of an endothelial marker, are determined by a specific ELISA to quantify the angiogenic response. It has been shown previously that these growth factors induce dose-dependent increases in weight, blood content and Tie-2 protein levels of this tissue growing (characterized histologically to contain fibroblasts and small blood vessels) around the chambers and that this response is blocked by neutralizing antibodies e.g. that specifically neutralize VEGF (see Wood J M et al., Cancer Res. 60(8), 2178-2189, (2000); and Schlaeppi et al., J. Cancer Res. Clin. Oncol. 125, 336-342, (1999)). With this model, inhibition can be shown in the case of compounds of the formula I at the concentrations given above.

In a preferred sense of the invention, a protein kinase modulation responsive disease is a disorder that responds in a for the treated individual beneficial way to modulation, especially inhibition, of the activity of a protein (preferably tyrosine) kinase, especially one characterized as being preferred above, where a compound of the formula I can be used, is one or more of a proliferative disease (meaning one dependent on (especially inadequate) activity of a protein kinase) including a hyperproliferative condition, such as one or more of leukemia, hyperplasia, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty. Further, a compound of the formula I may be used for the treatment of thrombosis and/or scleroderma.

Preferred is the use of a compound of the formula I in the therapy (including prophylaxis) of a proliferative disorder (especially which is responsive to modulation, especially inhibition, of the activity of a protein (preferably tyrosine) kinase, especially as mentioned as preferred herein) selected from tumor or cancer diseases, especially against preferably a benign or especially malignant tumor or cancer disease, more preferably solid tumors, e.g. carcinoma of the brain, kidney, liver, adrenal gland, bladder, breast, stomach (especially gastric tumors), ovaries, colon, rectum, prostate, pancreas, lung (e.g. small or large cell lung carcinomas), vagina, thyroid, sarcoma, glioblastomas, multiple myeloma or gastrointestinal cancer, especially colon carcinoma or colorectal adenoma, or a tumor of the neck and head, e.g. squamous carcinoma of the head and neck, including neoplasias, especially of epithelial character, e.g. in the case of mammary carcinoma; an epidermal hyperproliferation (other than cancer), especially psoriasis; prostate hyperplasia; or a leukemia.

A compound of formula I or its use makes it possible to bring about the regression of tumors and/or to prevent the formation of tumor metastases and the growth of (also micro)-metastases.

It is also possible to use the compounds of formula I in the treatment of diseases of the immune system insofar as several or, especially, individual protein (preferably tyrosine) kinases, especially those mentioned as preferred, are involved; furthermore, the compounds of formula I can be used also in the treatment of diseases of the central or peripheral nervous system where signal transmission by at least one protein (preferably tyrosine) kinase, especially selected from those protein tyrosine kinases mentioned as preferred, is involved.

In chronic myelogenous leukemia (CML), a reciprocally balanced chromosomal translocation in hematopoietic stem cells (HSCs) produces the BCR-ABL hybrid gene. The latter encodes the oncogenic Bcr-Abl fusion protein. Whereas ABL encodes a tightly regulated protein tyrosine kinase, which plays a fundamental role in regulating cell proliferation, adherence and apoptosis, the BCR-ABL fusion gene encodes as constitutively activated kinase which trans-forms HSCs to produce a phenotype exhibiting deregulated clonal proliferation, reduced capacity to adhere to the bone marrow stroma and a reduced apoptotic response to mutagenic stimuli, which enable it to accumulate progressively more malignant transformations. The resulting granulocytes fail to develop into mature lymphocytes and are released into the circulation, leading to a deficiency in the mature cells and increased infection susceptibility. ATP-competitive inhibitors of Bcr-Abl (or comparable mutated forms) have been described that prevent the kinase from activating mitogenic and anti-apoptotic pathways (e.g. P-3 kinase and STAT5), leading to the death of the BCR-ABL phenotype cells and thus providing an effective therapy against CML. The compounds of the formula I useful according to the present invention as Bcr-Abl inhibitors are thus especially appropriate for the therapy of diseases related to its overexpression, especially leukemias, such as leukemias, e.g. CML or ALL.

Angiogenesis is regarded as an absolute prerequisite for those tumors which grow beyond a maximum diameter of about 1-2 mm; up to this limit, oxygen and nutrients may be supplied to the tumor cells by diffusion. Every tumor, regardless of its origin and its cause, is thus dependent on angiogenesis for its growth after it has reached a certain size. Three principal mechanisms play an important role in the activity of angiogenesis inhibitors against tumors: 1) Inhibition of the growth of vessels, especially capillaries, into avascular resting tumors, with the result that there is no net tumor growth owing to the balance that is achieved between apoptosis and proliferation; 2) Prevention of the migration of tumor cells owing to the absence of blood flow to and from tumors; and 3) Inhibition of endothelial cell proliferation, thus avoiding the paracrine growth-stimulating effect exerted on the surrounding tissue by the endothelial cells normally lining the vessels.

Compounds of the formula I, in regard of their ability to inhibit KDR and especially Ephrin receptor kinase, and possibly other protein kinases, and thus to modulate angiogenesis, are especially appropriate for the use against diseases or disorders related to the inadequate activity of the corresponding receptor (preferably tyrosine) kinase, especially an overexpression thereof. Among these diseases, especially (e.g. ischemic) retinopathies, (e.g. age related) macula degeneration, psoriasis, obesity, hemangioblastoma, haemangioma, inflammatory diseases, such as rheumatoid or rheumatic inflammatory diseases, especially arthritis, such as rheumatoid arthritis, or other chronic inflammatory disorders, such as chronic asthma, arterial or post-transplantational atherosclerosis, endometriosis, and especially neoplastic diseases, for example so-called solid tumors (especially cancers of the gastrointestinal tract, the pancreas, breast, stomach, cervix, bladder, kidney, prostate, ovaries, endometrium, lung, brain, melanoma, Kaposi's sarcoma, squamous cell carcinoma of head and neck, malignant pleural mesothelioma, lymphoma or multiple myeloma) and further liquid tumors (e.g. leukemias) are especially important.

The compounds of the formula I are especially of use to prevent or treat diseases that are triggered by persistent angiogenesis, such as restenosis, e.g., stent-induced restenosis; Crohn's disease; Hodgkin's disease; eye diseases, such as diabetic retinopathy and neovascular glaucoma; renal diseases, such as glomerulonephritis; diabetic nephropathy; inflammatory bowel disease; malignant nephrosclerosis; thrombotic microangiopathic syndromes; (e.g. chronic) transplant rejections and glomerulopathy; fibrotic diseases, such as cirrhosis of the liver; mesangial cell-proliferative diseases; injuries of the nerve tissue; and for inhibiting the re-occlusion of vessels after balloon catheter treatment, for use in vascular prosthetics or after inserting mechanical devices for holding vessels open, such as, e.g., stents, as immunosuppressants, as an aid in scar-free wound healing, and for treating age spots and contact dermatitis.

Preferably, the invention relates to the use of compounds of the formula I, or pharmaceutically acceptable salts thereof, in the treatment of solid tumors as mentioned herein and/or of liquid tumors, e.g. leukemias, as mentioned herein.

Due to their protein kinase, such as Eph receptor kinase, modulating properties, the compounds of the formula I can also be used for stimulating or promoting neural regeneration (neuronal regeneration; neuroregeneration), such as axon regeneration, or inhibiting or reversing neural degeneration (neuronal degeneration; neurodegeneration). These uses represent further aspects of the instant invention.

The compounds of the formula I are, therefore, also useful in the treatment of protein kinase, such as Eph receptor kinase, modulation responsive conditions, diseases or disorders, where the stimulation or the promotion of neural regeneration (neuronal regeneration; neuroregeneration), such as axon regeneration, or the inhibition or the reversal of neural degeneration (neuronal degeneration; neurodegeneration) is desired, e.g. in the treatment of spinal cord injury, hypoxic conditions, traumatic brain injury, infarct, stroke, multiple sclerosis or other neurodegenerative conditions, diseases or disorders. These uses and methods of treatment represent further aspects of the instant invention.

Process of Manufacture

A compound of the formula I is prepared analogously to methods that, for other compounds, are in principle known in the art, so that for the novel compounds of the formula I the process is novel as analogy process, preferably by a) condensing a carbonic acid of the formula

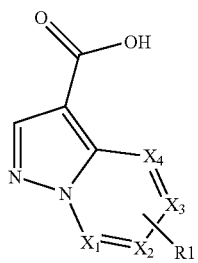

(II)

or a reactive derivative thereof, wherein R1, $X_1$, $X_2$, $X_3$ and $X_4$ are as defined for a compound of the formula I, with a compound of the formula

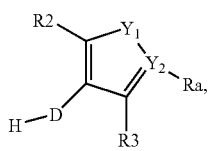

(III)

wherein R2, R3, D, $Y_1$, $Y_2$ and Ra are as defined for a compound of the formula I, or b) for the synthesis of a compound of the formula I, wherein R1 is unsubstituted or substituted alkyl, unsubstituted or substituted aryl, unsubstituted or substituted cycloalkyl or unsubstituted or substituted heterocyclyl, reacting a boronic acid of the formula

R1-B(A)$_2$  (IV), wherein R1 is unsubstituted or substituted alkyl, unsubstituted or substituted aryl (preferred), unsubstituted or substituted cycloalkyl or unsubstituted or substituted heterocyclyl (each bound via a C-Atom) and A is hydroxy or lower alkoxy or B(A)$_2$ is 9-borabicyclo[3.3.1]nonanyl or —B(CHCH$_3$CH(CH$_3$)$_2$)$_2$, with a compound of the formula

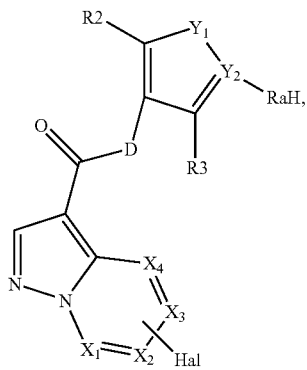

(V)

wherein R1, R2, R3, $X_1$, $X_2$, $X_3$, $X_4$, $Y_1$, $Y_2$, D and Ra are as defined for a compound of the formula I and Hal is halo, especially chloro, iodo or preferably bromo, or (perfluorinated C$_1$-C$_4$-alkyl)-sulfonyloxy;

and, if desired, transforming a compound of the formula I into a different compound of the formula I, transforming a salt of an obtainable compound of the formula I into the free compound or a different salt, transforming an obtainable free compound of the formula I into a salt thereof, and/or separating an obtainable mixture of isomers of a compound of the formula I into individual isomers.

Preferably, the condensation reaction a) with the carbonic acid of the formula X or XIV, respectively, or a reactive derivative thereof, takes place with a reactive carbonic acid derivative that can be used as such, e.g. with the reactive carbonic acid derivative in the form of a symmetric or mixed anhydride, an active ester or a carbonic acid halide, e.g. the acid chloride, e.g. in the presence of a tertiary nitrogen base, such as a tri-lower alkylamine or pyridine, or can be formed in situ, e.g. by condensation in the presence of reagents that form reactive esters in situ. The reaction is, e.g., carried out by dissolving the carbonic acids and the corresponding amine in a suitable solvent, for example a halogenated hydrocarbon, such as methylene chloride, N,N-dimethylformamide, N,N-dimethylacetamide, N-methyl-2-pyrrolidone, methylene chloride, or a mixture of two or more such solvents, and by the addition of a suitable base, for example triethylamine, diisopropylethylamine (DIEA) or N-methylmorpholine and, if the reactive derivative of the acid of the formula II is formed in situ, a suitable coupling agent that forms a preferred reactive derivative of the carbonic acid of formula III in situ, for example dicyclohexylcarbodiimide/1-hydroxybenzotriazole (DCC/HOBT); bis(2-oxo-3-oxazolidinyl)phosphinic chloride (BOPCI); O-(1,2-dihydro-2-oxo-1-pyridyl)-N,N,N',N'-N-'-tetramethyluronium tetrafluoroborate (TPTU); O-benzotriazol-1-yl)-N,N,N',N'-tetramethyluronium tetrafluoroborate (TBTU); (benzotriazol-1-yloxy)-tripyrrolidinophosphonium-hexafluorophosphate (PyBOP), 1-(3-dimethylaminopropyl)-3-ethylcarbodiimide hydrochloride/hydroxybenzotriazole or/1-hydroxy-7-azabenzotriazole (EDC/HOBT or EDC/HOAt) or HOAt alone, or with (1-chloro-2-methyl-propenyl)-dimethylamine. For review of some other possible coupling agents, see e.g. Klauser; Bodansky, *Synthesis* 1972, 453-463. The reaction mixture is preferably stirred at a temperature of between approximately −20 and 50° C., especially between 0° C. and 30° C., e.g. at room temperature.

The reaction under b) takes place under Suzuki coupling or comparable conditions, e.g. in the presence of a palladium catalyst, such as Pd(PPh$_3$)$_4$ wherein Ph is phenyl or Pd(dppf)Cl$_2$ wherein dppf is 1,1'-bis(diphenylphosphino)ferrocene, and a base, such as an alkali metal carbonate, e.g. sodium carbonate, an alkali metal alcoholate, such as sodium ethoxide, a tertiary nitrogen base, such as triethylamine, or an alkalimetal phosphate, such as potassium phosphate, in the presence or absence of an appropriate solvent, e.g. an ether, such as tetrahydrofurane or 1,4-dioxane, a hydrocarboyn, e.g. toluene, and/or water, e.g. at elevated temperatures, for example from 30 to 30° C. to the reflux temperature or at higher temperatures in a closed pressure-compatible reaction vessel.

Optional Reactions and Conversions

A compound of the formula I may be converted into a different compounds of the formula I, e.g. after one of the reactions a) or b) mentioned above is completed.

For example, in a compound of the formula I wherein R1 is halo-aryl, such as bromo-aryl, e.g. bromophenyl, the halogen may be replaced with a substituent bound via a nitrogen atom, for example with morpholino, by reaction with a corresponding primary or secondary amine, such as morpholine, in the presence of a strong base, such as an alkaline metal alcoxide, e.g. potassium tert-butoxide, and an appropriate coupling catalyst, e.g. 2-(dimethylamino-)-2-biphenylyl-palladium (II) chloride dinorbornylphosphin complex, in an appropriate solvent or solvent mixture, e.g. an ether, such as tetrahydrofurane, at preferably elevated .temperatures, e.g. from 30° C. to the reflux temperature.

Yet another example of a conversion of a compound of the formula I can be given where a nitro substitutent is present in substituted aryl R1—such a nitro substituent can be reduced to a corresponding amino substituent, for example by catalytic hydrogenation, e.g. in the presence of Raney-Ni, in an appropriate solvent or solvent mixture, e.g. an alcohol, such as methanol or ethanol, e.g. at temperatures from 0 to 50° C.

An amino substituent in a compound of the formula I (especially amino as substituent of aryl R1 in formula I) can be converted into a mono-, di- or tri-alkylated amino (in the latter case quaternary) substituent by reaction with a corresponding alkyl halogenide, e.g. methyl iodide, preferably in the presence of a tertiary nitrogen base, such as triethylamine, in an appropriate solvent or solvent mixture, e.g. an N,N-di-(lower alkyl)-lower alkanoylamide, such as N,N-dimethylformamide, preferably at temperatures from 20 to 80° C.

In a compound of the formula I wherein R1 is aryl that is substituted by iodo or bromo and possibly one or more other substitutents, such as trifluoro, e.g. where R1 is 4-iodo-3-trifluoromethylphenyl, the bromo or iodo may be replaced with substituted or unsubstituted aryl, such as 4-cyanophenyl, by coupling reaction with the corresponding substituted or unsubstituted arylboronic acid of the formula

Ar—B(OH)$_2$  (IV), wherein Ar is unsubstituted or substituted aryl, in the presence of a catalyst, especially PdCl$_2$(dppf) and preferably also a base, such as an alkali metal carbonate, e.g. sodium carbonate, in an appropriate solvent or solvent mixture, e.g. toluene/water, at, for example, elevated temperatures, e.g. between 30° C. and the (preferred) reflux temperature.

Salts of compounds of formula I having at least one salt-forming group may be prepared in a manner known per se. For example, a salt of a compound of formula I having acid groups may be formed by treating the compound with a metal compound, such as an alkali metal salt of a suitable organic carboxylic acid, e.g. the sodium salt of 2-ethylhexanoic acid, with an organic alkali metal or alkaline earth metal compound, such as the corresponding hydroxide, carbonate or hydrogen carbonate, such as sodium or potassium hydroxide, carbonate or hydrogen carbonate, with a corresponding calcium compound or with ammonia or a suitable organic amine, stoichiometric amounts or only a small excess of the salt-forming agent preferably being used. An acid addition salt of compounds of formula I can be obtained in customary manner, e.g. by treating a compound of the formula I with an acid or a suitable anion exchange reagent. Internal salts of compounds of formula I containing acid and basic salt-forming groups, e.g. a free carboxy group and a free amino group, may be formed, e.g. by the neutralization of salts, such as acid addition salts, to the isoelectric point, e.g. with weak bases, or by treatment with ion exchangers.

A salt of a compound of the formula I can be converted in customary manner into the free compound; a metal or ammonium salt can be converted, for example, by treatment with a suitable acid, and an acid addition salt, for example, by treatment with a suitable basic agent. In both cases, suitable ion exchangers may be used.

Stereoisomeric mixtures, e.g. mixtures of diastereomers, can be separated into their corresponding isomers in a manner known per se by means of appropriate separation methods. Diastereomeric mixtures for example may be separated into their individual diastereomers by means of fractionated crystallization, chromatography, solvent distribution, and similar procedures. This separation may take place either at the level of one of the starting compounds or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

Intermediates and final products can be worked up and/or purified according to standard methods, e.g. using chromatographic methods, distribution methods, (re-) crystallization, and the like.

Starting Materials

Starting materials are either known in the art, commercially available or they can be prepared according to methods that are known in the art. Protecting groups, if not specifically mentioned, can be introduced and removed at appropriate steps in order to prevent functional groups, the reaction of which is not desired in the corresponding reaction step or steps, employing protecting groups, methods for their introduction and their removal are as described above or below, e.g. in the references mentioned under "General Process Conditions". The person skilled in the art will readily be able to decide whether and which protecting groups are useful or required.

Where in the starting materials R1, R2, R3, $X_1$, $X_2$, $X_3$, $X_4$, $Y_1$, $Y_2$, Ra, D, R6, A, R4, $Z_1$, $Z_2$, $Z_3$, $R_5$ and n are used, these symbols preferably have the meanings given for a compound of the formula I, if not indicated otherwise or dictated otherwise by the context.

Starting materials can, for example, preferably be prepared as follows:

For example, a starting material of the formula II wherein R1 unsubstituted or substituted alkyl, unsubstituted or substituted aryl, unsubstituted or substituted cycloalkyl or unsubstituted or substituted heterocyclyl (and is bound to a ring carbon atom) can be prepared from a (if required, at the carboxy group protected) compound of the formula

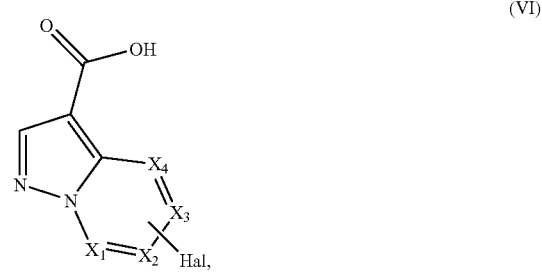

(VI)

wherein Hal is halo, especially chloro, iodo or preferably bromo, or (perfluorinated $C_1$-$C_4$-alkyl)-sulfonyloxy, by reaction with a compound of the formula IV as defined above under reaction b) under preferred reaction conditions as described above for reaction b), followed by removal of protecting groups no longer required or desired.

A compound of the formula III wherein Ra is a moiety of the formula IA as defined for a compound of the formula I can and D is NH can, for example, be prepared as follows:

A compound of the formula III wherein D is NH, $Y_2$ is C and Ra is a moiety of the formula IA as defined above wherein A is C(=O)—N(R4) can preferably be obtained by condensing a carbonic acid of the formula

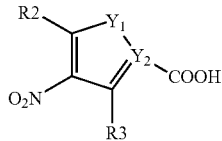
(VII)

or a reactive derivative thereof, wherein $Y_2$ is C, with an amine of the formula

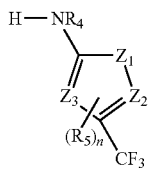
(VIII)

to give a compound of the formula

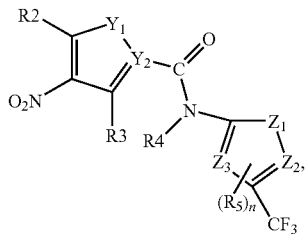
(IX)

wherein $Y_2$ is C.

A compound of the formula III wherein D is NH can then be obtained in that a compound of the formula IX, obtained as before or by any other method, is reduced, e.g. by catalytic hydrogenation, for example in the presence of Raney-Ni in an appropriate solvent or solvent mixture, e.g. an alcohol, such as methanol or ethanol, at temperatures e.g. from 0 to 50° C., to the corresponding compound of the formula III wherein in Ra A is C(=O)—N(R4) and R6 is hydrogen—which latter may then, if desired, be converted to unsubstituted or substituted alkyl R6 by alkylation with an appropriate halogenide of the formula R6-Hal (X), wherein R6 is unsubstituted or substituted alkyl and Hal is halo, especially bromo or iodo, under customary alkylation conditions.

Alternatively, a corresponding compound of the formula III wherein D is O or S may be obtained by condensing a carbonic acid compound analogous to that of the formula VIII above, or a reactive derivative thereof, but wherein instead of the nitro group (preferably protected) hydroxy or (preferably protected) mercapto is present, with an amine of the formula VIII as described above and removing the protecting groups.

A compound of the formula III wherein D is NH, O or S, $Y_2$ is C and Ra is a moiety of the formula IA as defined above wherein A is N(R4)-C(=O) can be obtained by condensing a carbonic acid of the formula

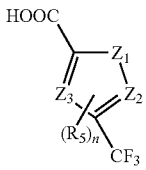
(XI)

or a reactive derivative thereof, with an amino compound of the formula

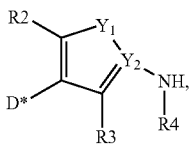
(XII)

wherein $Y_2$ is C, D* is (preferably protected) amino, (preferably protected) hydroxy, (preferably protected) mercapto or nitro, to give a corresponding compound of the formula

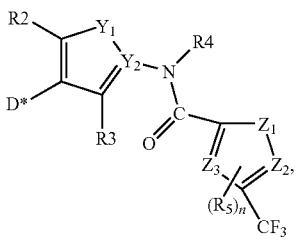
(XIII)

wherein D* is (preferably protected) amino, (preferably protected) hydroxy, (preferably protected) mercapto or nitro and Y2 is C, which can then be converted to a corresponding compound of the formula III in that either, if D* is nitro, the nitro is reduced to amino, e.g. by catalytic hydrogenation, for example in the presence of Raney-Ni in an appropriate solvent or solvent mixture, e.g. an alcohol, such as methanol or ethanol, at temperatures e.g. from 0 to 50° C., to the corresponding compound of the formula III wherein, in Ra, A is N(R4)-C(=O) and R6 is hydrogen—which latter may then, if desired, be converted to unsubstituted or substituted alkyl R6 by alkylation with an appropriate halogenide of the formula X as defined above, or (a) protecting group(s) is or are removed.

The reactive derivatives of the carbonic acid of the formula VII or XI, as well as the reaction conditions for the condensation, are preferably chosen in analogy to the reaction conditions described above for process a).

Other starting materials, also those mentioned as starting materials of intermediates above, are known in the art, commercially available and/or can be prepared according to standard procedures, e.g. in analogy to or by methods described in the Examples.

General Process Conditions

The following applies in general to all processes mentioned hereinbefore and hereinafter, while reaction conditions specifically mentioned above or below are preferred:

In any of the reactions mentioned hereinbefore and hereinafter, protecting groups may be used where appropriate or desired, even if this is not mentioned specifically, to protect functional groups that are not intended to take part in a given reaction, and they can be introduced and/or removed at appropriate or desired stages. Reactions comprising the use of protecting groups are therefore included as possible also in cases where reactions without specific mentioning of protection and/or deprotection are described in this specification.

Within the scope of this disclosure only a readily removable group that is not a constituent of the particular desired end product of formula I is designated a "protecting group", unless the context indicates otherwise. The protection of functional groups by such protecting groups, the protecting groups themselves, and the reactions appropriate for their removal are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H. -D. Jakubke and H. Jeschkeit, "Aminosacuren, Peptide, Proteine" (*Amino acids, Peptides, Proteins*), Verlag Chemie, Weinheim, Deerfield Beach, and Basel 1982, and in Jochen Leh-mann, "Chemie der Kohlenhydrate: Monosaccharide und Derivate" (*Chemistry of Carbohydrates: Monosaccharides and Derivatives*), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

All the above-mentioned process steps can be carried out under reaction conditions that are known per se, preferably those mentioned specifically, in the absence or, customarily, in the presence of solvents or diluents, preferably solvents or diluents that are inert towards the reagents used and dissolve them, in the absence or presence of catalysts, condensation or neutralizing agents, for example ion exchangers, such as cation exchangers, e.g. in the H$^+$ form, depending on the nature of the reaction and/or of the reactants at reduced, normal or elevated temperature, for example in a temperature range of from about −100° C. to about 190° C., preferably from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, e.g. as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of these, for example aqueous solutions, unless otherwise indicated in the description of the processes. Such solvent mixtures may also be used in working up, for example by chromatography or partitioning.

The invention relates also to those forms of the process in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention is produced under the process conditions and processed further in situ. In the process of the present invention those starting materials are preferably used which result in compounds of formula I described as being preferred. The invention also relates to novel intermediates and/or starting materials. Special preference is given to reaction conditions that are identical or analogous to those mentioned in the Examples.

PREFERRED EMBODIMENTS ACCORDING TO THE INVENTION

In the preferred embodiments as well as in preceding and following embodiments of more general scope, also in the claims, any one or more or all general expressions can be replaced by the corresponding more specific definitions provided above and below, thus yielding stronger preferred embodiments of the invention.

The invention in a preferred embodiment relates to a compound of the formula I, wherein R1 is hydrogen, halo, unsubstituted or substituted alkyl, unsubstituted or substituted aryl, unsubstituted or substituted cycloalkyl or unsubstituted or substituted heterocyclyl;

each of R3 and R3 is, independently of the other, hydrogen, halo, $C_1$-$C_4$.alkyl, trifluoromethyl, $C_1$-$C_4$.alkoxy or cyano;

$X_1$, $X_2$, $X_3$ and $X_4$ are CH;

D is N(R6), wherein R6 is acyl or unsubstituted or substituted alkyl;

$Y_1$ is HC=CH;

$Y_2$ is C;

Ra is hydrogen if R1 is unsubstituted alkyl with more 5 or more carbon atoms, substituted alkyl, unsubstituted or substituted aryl, unsubstituted or substituted cycloalkyl or unsubstituted or substituted heterocyclyl; or, if R1 is hydrogen, halo or $C_1$-$C_4$-alkyl, is a moiety of the formula IA given above, wherein the dotted line means the bond binding to the rest of the molecule of the formula I, A is C(=O)—N(R4) or N(R4)-C(=O), wherein R4 is hydrogen or unsubstituted or substituted alkyl, $Z_1$ is CH=CH, $Z_2$ is N or CH, $Z_3$ is CH, each $R_5$ is, independently of the others, a substituent, and n is 0, 1 or 2, in free form or in salt form.

The invention, in another preferred embodiment, relates to a compound of the formula I wherein
R1 is hydrogen, halo or $C_1$-$C_4$-alkyl;
each of R2 and R3 is, independently of the other, hydrogen, halo, $C_1$-$C_4$-alkyl, trifluoromethyl, $C_1$-$C_4$-alkoxy or cyano,
$X_1$, $X_2$, $X_3$ and $X_4$ are CH or up to two of them can be N;
D is N(R6) (preferred), O or S,
  wherein R6 is hydrogen, acyl or unsubstituted or substituted alkyl,
$Y_1$ is O, S, NH, $CH_2$, N=CH, CH=N or CH=CH;
$Y_2$ is C;
Ra is a moiety of the formula

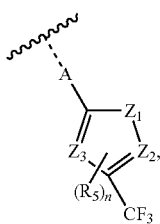

(IA)

wherein the dotted line means the bond binding to the rest of the molecule of the formula I (which is indicated by the wave line),
A is C(=O)—N(R4) or N(R4)-C(=O),
  wherein R4 is hydrogen or unsubstituted or substituted alkyl,
$Z_1$ is O, S, NH, $CH_2$, CH=N, N=CH or CH=CH,
$Z_2$ is nitrogen or CH,
$Z_3$ is CH or N,
each $R_5$ present is, independently of the others, a substituent and
n is 0, 1 or 2, in free form or in salt form.

In an alternative preferred embodiment, the invention relates to a compound of the formula I wherein
R1 is unsubstituted alkyl with 5 or more carbon atoms or substituted alkyl, unsubstituted or substituted aryl, unsubstituted or substituted cycloalkyl or unsubstituted or substituted heterocyclyl;
each of R2 and R3 is, independently of the other, hydrogen, halo, $C_1$-$C_4$-alkyl, trifluoromethyl, $C_1$-$C_4$-alkoxy or cyano,
$X_1$, $X_2$, $X_3$ and $X_4$ are CH or up to two of them can be N;
D is N(R6) (preferred), O or S,
  wherein R6 is hydrogen, acyl or unsubstituted or substituted alkyl,
$Y_1$ is O, S, NH, $CH_2$, N=CH, CH=N or CH=CH;
$Y_2$ is C or N;
Ra is absent or, if $Y_2$ is C, is hydrogen, in free form or in salt form.

The invention relates also to pharmaceutical preparations, the use of a compound in the treatment or for the manufacture of a pharmaceutical preparation useful in the treatment of a disease responsive to protein kinase modulation (especially inhibition), a method of treatment comprising administering to an individual (animal or preferably human) in need of such treatment a compound of the formula I or a pharmaceutically acceptable salt thereof in an amount that is efficient in the treatment of a disease responsive to modulation (especially inhibition) of a protein kinase (especially a protein tyrosine kinase), and a process for the manufacture of a compound of the formula I, or a salt thereof; in each case preferably the compound of the formula I, or the (pharmaceutically acceptable) salt thereof, is a compound characterized as preferred hereinabove or hereinbelow.

The invention also preferably relates to the embodiments given in the (especially dependent) claims. All the claims are therefore included by reference herein.

The invention related especially to a compound of the formula I given in the Examples, or a pharmaceutically acceptable salt thereof, or its use according to the invention, as well as the processes and novel starting materials and intermediates mentioned in the Examples.

Pharmaceutical Compositions

The invention relates also to pharmaceutical compositions comprising a (preferably novel) compound of formula I, to their use in the therapeutic (in a broader aspect of the invention also prophylactic) treatment or a method of treatment of a disease or disorder that depends on inadequate protein (especially tyrosine) kinase activity, especially the preferred disorders or diseases mentioned above, to the compounds for said use and to pharmaceutical preparations and their manufacture, especially for said uses. More generally, pharmaceutical preparations are useful in case of compounds of the formula I.

The pharmacologically acceptable compounds of the present invention may be present in or employed, for example, for the preparation of pharmaceutical compositions that comprise an effective amount of a compound of the formula I, or a pharmaceutically acceptable salt thereof, as active ingredient together or in admixture with one or more inorganic or organic, solid or liquid, pharmaceutically acceptable carriers (carrier materials).

The invention relates also to a pharmaceutical composition that is suitable for administration to a warm-blooded animal, especially a human (or to cells or cell lines derived from a warm-blooded animal, especially a human, e.g. lymphocytes), for the treatment (this, in a broader aspect of the invention, also including prevention of (=prophylaxis against)) a disease that responds to inhibition of protein (especially tyrosine) kinase activity, comprising an amount of a compound of formula I or a pharmaceutically acceptable salt thereof, preferably which is effective for said inhibition, together with at least one pharmaceutically acceptable carrier.

The pharmaceutical compositions according to the invention are those for enteral, such as nasal, rectal or oral, or parenteral, such as intramuscular or intravenous, administration to warm-blooded animals (especially a human), that comprise an effective dose of the pharmacologically active ingredient, alone or together with a significant amount of a pharmaceutically acceptable carrier. The dose of the active ingredient depends on the species of warm-blooded animal, the body weight, the age and the individual condition, individual pharmacokinetic data, the disease to be treated and the mode of administration.

The invention relates also to method of treatment for a disease that responds to inhibition of a disease that depends on inadequate activity of a protein (especially tyrosine) kinase; which comprises administering a prophylactically or especially therapeutically effective amount of a compound of formula I, or a pharmaceutically acceptable salt thereof, especially to a warm-blooded animal, for example a human, that, on account of one of the mentioned diseases, requires such treatment.

The dose of a compound of the formula I or a pharmaceutically acceptable salt thereof to be administered to warm-blooded animals, for example humans of approximately 70 kg body weight, preferably is from approximately 3 mg to approximately 10 g, more preferably from approximately 10 mg to approximately 1.5 g, most preferably from about 100 mg to about 1000 mg/person/day, divided preferably into 1-3 single doses which may, for example, be of the same size. Usually, children receive half of the adult dose.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragées, tablets or capsules.

The pharmaceutical compositions of the present invention are prepared in a manner known per se, for example by means of conventional dissolving, lyophilizing, mixing, granulating or confectioning processes.

Solutions of the active ingredient, and also suspensions, and especially isotonic aqueous solutions or suspensions, are preferably used, it being possible, for example in the case of lyophilized compositions that comprise the active ingredient alone or together with a carrier, for example mannitol, for such solutions or suspensions to be produced prior to use. The pharmaceutical compositions may be sterilized and/or may comprise excipients, for example preservatives, stabilizers, wetting and/or emulsifying agents, solubilizers, salts for regulating the osmotic pressure and/or buffers, and are prepared in a manner known per se, for example by means of conventional dissolving or lyophilizing processes. The said solutions or suspensions may comprise viscosity-increasing substances, such as sodium carboxymethylcellulose, carboxymethylcellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as the acid component a long-chained fatty acid having from 8-22, especially from 12-22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brasidic acid or linoleic acid, if desired with the addition of antioxidants, for example vitamin E, β-carotene or 3,5-di-tert-butyl-4-hydroxytoluene. The alcohol component of those fatty acid esters has a maximum of 6 carbon atoms and is a mono- or poly-hydroxy, for example a mono-, di- or tri-hydroxy, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Paris), "Miglyol 812" (triglyceride of saturated fatty acids with a chain length of C8 to C12, Hüls AG, Germany), but especially vegetable oils, such as cottonseed oil, almond oil, olive oil, castor oil, sesame oil, soybean oil and groundnut oil.

The injection or infusion compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, dragée cores or capsules. It is also possible for them to be incorporated into plastics carriers that allow the active ingredients to diffuse or be released in measured amounts.

Suitable carriers are especially fillers, such as sugars, for example lactose, saccharose, mannitol or sorbitol, cellulose preparations and/or calcium phosphates, for example tricalcium phosphate or calcium hydrogen phosphate, and binders, such as starch pastes using for example corn, wheat, rice or potato starch, gelatin, tragacanth, methylcellulose, hydroxypropylmethylcellulose, sodium carboxymethylcellulose and/or polyvinylpyrrolidone, and/or, if desired, disintegrators, such as the above-mentioned starches, and/or carboxymethyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and soft sealed capsules made of gelatin and a plasticizer, such as glycerol or sorbitol. The dry-filled capsules may comprise the active ingredient in the form of granules, for example with fillers, such as lactose, binders, such as starches, and/or glidants, such as talc or magnesium stearate, and if desired with stabilizers. In soft capsules the active ingredient is preferably dissolved or suspended in suitable oily excipients, such as fatty oils, paraffin oil or liquid polyethylene glycols, it being possible also for stabilizers and/or antibacterial agents to be added. Dyes or pigments may be added to the tablets or dragée coatings or the capsule casings, for example for identification purposes or to indicate different doses of active ingredient.

A compound of the formula I may also be used to advantage in combination with other biologically active agents, preferentially with other antiproliferative agents. Such antiproliferative agents include, but are not limited to aromatase inhibitors; antiestrogens; topoisomerase I inhibitors; topoisomerase II inhibitors; microtubule active agents; alkylating agents; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; agents used in the treatment of hematologic malignancies; compounds which target, decrease or inhibit the activity of Flt-3; Hsp90 inhibitors; and temozolomide (TEMODAL®).

The term "aromatase inhibitor" as used herein relates to a compound which inhibits the estrogen production, i.e. the conversion of the substrates adrostenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g. under the trademark ARO-MASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active agent" relates to microtubule stabilizing, microtubule destabilizing agents and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or a derivative thereof. Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating agent" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "histone deacetylase inhibitors" or "HDAC inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl) ethyl]-amino]methyl]phenyl]-2E-2-propenamide, N-hydroxy-3-[4-[[[2-(2-methyl-1H-indol-3-yl)-ethyl]-amino] methyl]phenyl]-2E-2-propenamide and pharmaceutically acceptable salts thereof. It further especially includes Suberoylanilide hydroxamic acid (SAHA).

The term "antineoplastic antimetabolite" includes, but is not limited to, 5-fluorouracil (5-FU); capecitabine; gemcitabine; DNA demethylating agents, such as 5-azacytidine and decitabine; methotrexate; edatrexate; and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR. Also included is the monoclonal antibody trastuzumab which can be administered, e.g., in the form as it is marketed, e.g. under the trademark HERCEPTIN.

The term "platin compound" as used herein includes, but is not limited to, carboplatin, cisplatin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity and further anti-angiogenic compounds" as used herein includes, but is not limited to: protein tyrosine kinase and/or serine and/or threonine kinase inhibitors or lipid kinase inhibitors, e.g.:
a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668, and GFB-111;
b) compounds targeting, decreasing or inhibiting the activity of the fibroblast growth factor-receptors (FGFR);

c) compounds targeting, decreasing or inhibiting the activity of the insulin-like growth factor I receptor (IGF-IR), especially compounds which inhibit the IGF-IR, such as those compounds disclosed in WO 02/092599;
d) compounds targeting, decreasing or inhibiting the activity of the Trk receptor tyrosine kinase family;
e) compounds targeting, decreasing or inhibiting the activity of the Axl receptor tyrosine kinase family;
f) compounds targeting, decreasing or inhibiting the activity of the c-Met receptor;
g) compounds targeting, decreasing or inhibiting the activity of the c-Kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;
h) compounds targeting, decreasing or inhibiting the activity of members of the c-Abl family and their gene-fusion products (e.g. BCR-Abl kinase), such as compounds which target decrease or inhibit the activity of c-Abl family members and their gene fusion products, e.g. a N-phenyl-2-pyrimidine-amine derivative, e.g. imatinib; PD180970; AG957; NSC 680410; or PD173955 from ParkeDavis;
i) compounds targeting, decreasing or inhibiting the activity of members of the protein kinase C (PKC) and Raf family of serine/threonine kinases, members of the MEK, SRC, JAK, FAK, PDK and Ras/MAPK family members, or PI(3) kinase family, or of the PI(3)-kinase-related kinase family, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; PD184352 or QAN697 (a P13K inhibitor);
j) compounds targeting, decreasing or inhibiting the activity of a protein-tyrosine kinase, such as imatinib mesylate (GLIVEC/GLEEVEC) or tyrphostin. A tyrphostin is preferably a low molecular weight (Mr<1500) compound, or a pharmaceutically acceptable salt thereof, especially a compound selected from the benzylidenemalonitrile class or the S-arylben-zenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer, Tyrphostin AG 555; AG 494; Tyrphostin AG 556, AG957 and adaphostin (4-{[(2,5-dihydroxyphenyl) methyl]amino}-benzoic acid adamantyl ester; NSC 680410, adaphostin); and
k) compounds targeting, decreasing or inhibiting the activity of the epidermal growth factor family of receptor tyrosine kinases (EGFR, ErbB2, ErbB3, ErbB4 as homo- or heterodimers), such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (HerpetinR), cetuximab, Iressa, erlotinib (Tarceva™), CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g. inhibitors of phosphatase 1, phosphatase 2A, PTEN or CDC25, e.g. okadaic acid or a derivative thereof.

Compounds which induce cell differentiation processes are e.g. retinoic acid, α- γ- or δ-tocopherol or α- γ- or δ-tocotrienol.

The term "cyclooxygenase inhibitor" as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

Immunomodulatory drugs which are prone to be useful in combination with a compound of the present invention include e.g.
   mediators, e.g. inhibitors, of mTOR activity, including rapamycin of formula

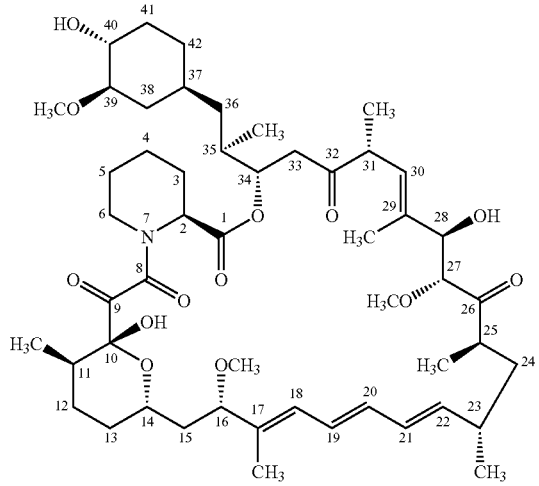

and rapamycin derivatives, e.g. including
40-O-alkyl-rapamycin derivatives, such as 40-O-hydroxyalkyl-rapamycin derivatives, such as 40-O-(2-hydroxy)-ethyl-rapamycin (everolimus),
32-deoxo-rapamycin derivatives and 32-hydroxy-rapamycin derivatives, such as 32-deoxorapamycin,
16-O-substituted rapamycin derivatives such as 16-pent-2-ynyloxy-32-deoxorapamycin, 16-pent-2-ynyloxy-32(S or R)-dihydro-rapamycin, 16-pent-2-ynyloxy-32(S or R)-dihydro-40-O-(2-hydroxyethyl)-rapamycin, rapamycin derivatives which are acylated at the oxygen group in position 40, e.g. 40-[3-hydroxy-2-(hydroxymethyl)-2-methylpropanoate]-rapamycin (also known as CCI779), rapamycin derivatives which are substituted in 40 position by heterocyclyl, e.g. 40-epi-(tetrazolyl)-rapamycin (also known as ABT578), the so-called rapalogs, e.g. as disclosed in WO9802441 or WO0114387, e.g. such as 40-O-dimethylphosphinyl-rapamycin, including AP23573, and compounds disclosed under the name biolimus (biolimus A9), including 40-O-(2-ethoxy)ethyl-rapamycin, and compounds disclosed under the name TAFA-93, preferably 40-O-(2-hydroxy)-ethyl-rapamycin, CCI779, ABT578, or AP23573, more preferably 40-O-(2-hydroxy)-ethyl-rapamycin (everolimus).

Rapamycin and other rapamycin derivatives may be administered as appropriate, e.g. in dosages which are known for rapamycin or rapamycin derivatives, e.g. everolimus may be administered in dosages from 0.1 mg up to 15 mg, such as 0.1 mg to 10 mg. e.g. 0.1 mg, 0.25 mg, 0.5 mg, 0.75 mg, 1 mg, 2.5 mg, 5 mg, or 10 mg, e.g. in the form of (dispersible) tablets; e.g. a weekly dosage may include up to 70 mg depending on the disease being treated. Other rapamycin derivatives may be administered in similar dosage ranges.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA™. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "heparanase inhibitor" as used herein refers to compounds which target, decrease or inhibit heparin sulphate degradation. The term includes, but is not limited to, PI-88.

The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor", e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. PS-341 and MLN 341.

The term "matrix metalloproteinase inhibitor" or ("MMP inhibitor") as used herein includes, but is not limited to collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "agents used in the treatment of hematologic malignancies" as used herein includes, but is not limited to FMS-like tyrosine kinase inhibitors e.g. compounds targeting, decreasing or inhibiting the activity of Flt-3; interferon, 1-b-D-arabinofuransylcytosine (ara-c) and bisulfan; and ALK inhibitors e.g. compounds which target, decrease or inhibit anaplastic lymphoma kinase.

The term "compounds which target, decrease or inhibit the activity of Flt-3" are especially compounds, proteins or antibodies which inhibit Flt-3, e.g. PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteasome pathway. Compounds targeting, decreasing or inhibiting the intrinsic ATPase activity of HSP90 are especially compounds, proteins or antibodies which inhibit the ATPase activity of HSP90 e.g., 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to trastuzumab (Herceptin™), Trastuzumab-DM1, bevacizumab (Avastin™), rituximab (Rituxan®), PRO64553 (anti-CD40) and 2C4 Antibody. By antibodies is meant e.g. intact monoclonal antibodies, polyclonal antibodies, multispecific antibodies formed from at least 2 intact antibodies, and antibodies fragments so long as they exhibit the desired biological activity. For the treatment of acute myeloid leukemia (AML), compounds of formula I can be used in combination with standard leukemia therapies, especially in combination with therapies used for the treatment of AML. In particular, compounds of formula I can be administered in combination with e.g. farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The structure of the active agents identified by code nos., generic or trade names may be taken from the actual edition of the standard compendium "The Merck Index" or from databases, e.g. Patents International (e.g. IMS World Publications).

The above-mentioned compounds, which can be used in combination with a compound of the formula I, can be prepared and administered as described in the art such as in the documents cited above.

A compound of the formula I may also be used to advantage in combination with known therapeutic processes, e.g., the administration of hormones or especially radiation.

A compound of formula I may in particular be used as a radiosensitizer, especially for the treatment of tumors which exhibit poor sensitivity to radiotherapy.

By "combination", there is meant either a fixed combination in one dosage unit form, or a kit of parts for the combined administration where a compound of the formula I and a combination partner may be administered independently at the same time or separately within time intervals that especially allow that the combination partners show a cooperative, e.g. synergistic, effect, or any combination thereof.

EXAMPLES

The following examples illustrate the invention without limiting the scope thereof.

Temperatures are measured in degrees Celsius. Unless otherwise indicated, the reactions take place at room temperature.

The $R_f$ values in TLC indicate the ratio of the distance moved by each substance to the distance moved by the eluent front. $R_f$ values for TLC are measured on 5×10 cm TLC plates, silica gel $F_{254}$, Merck, Darmstadt, Germany; the solvent systems are marked in the examples as follows:
*10% methanol/90% methylene chloride ($CH_2Cl_2$)
**50% hexane/50% ethyl acetate
***100% methylene chloride ($CH_2Cl_2$)

If not indicated otherwise, the analytical HPLC conditions are as follows:
Column: Column Engineering, Inc., Matrix, 3 μm C18 150× 4.6 mm (Lot # 205) Detection by UV absorption at 215 and 254 nm. The column temperature is 35° C. and the retention times ($t_R$) are given in minutes. Flow rate: 1 mL/min. Gradient: water (0.1% TFA)/acetonitrile (0.1% TFA)=98/2 for 1 min. to 100% acetonitrile (0.1% TFA) in 10 min. Stay at 100% for 2 min (total run time: 13 min.)
Abbreviations
HPLC High Performance Liquid Chromatography
Isolute=Isolute® HM-N by International Solvent Technology
mL milliliter(s)
min minute(s)
MS-ES electrospray mass spectrometry
$R_f$ ratio of fronts in TLC
RT room temperature
TFA trifluoro acetic acid
TLC thin layer chromatography
$t_R$ retention time
UV Ultraviolet
Starting Materials:
General Procedure for the Synthesis of Aniline Building Blocks (Illustrated with the Formula and Educts for N-(3-amino-4-methyl-phenyl)-3-trifluoromethyl-benzamide):

The compound shown on the left above, N-(3-amino-4-methyl-phenyl)-3-trifluoromethyl-benzamide, is obtained by hydrogenation of the corresponding nitro-compound (N-(4-methyl-3-nitro-phenyl)-3-trifluoromethyl-benzamide) with Raney-Nickel in methanol at room temperature. The product is obtained in high yield. The intermediate nitro compound (A), N-(3-nitro-4-methyl-phenyl)-3-trifluoromethyl-benzamide, is obtained by reaction of 4-methyl-3-nitro-phenylamine (B) and 3-trifluoromethyl-benzoyl chloride (C) in methylenehloride at room temperature and using triethylamine. The intermediate (A) is obtained in good yield. Similar and different anilines have been described before in the literature and patents (e.g. CAS No. 30069-31-9). For coupling, the corresponding acid chlorides are used.

The reversed 3-amino-benzamide derivatives, 3-amino-4-methyl-N-(3-trifluoromethylphenyl)-benzamide and 3-amino-N-(4-methoxy-3-trifluoromethyl-phenyl)-4-methylbenzamide, are synthesized according the same procedure using the corresponding commercially available starting materials.

Example 1

Pyrazolo[1,5-a]pyridine-3-carboxylic acid [2-methyl-5-(3-trifluoromethyl-benzoylamino)-phenyl]-amide Pyrazolo[1,5-a]pyridine-3-carbonylchloride (100 mg, 0.55 mmol, Maybridge Lot # 291259) and N-(3-amino-4-methyl-phenyl)-3-trifluoromethyl-benzamide (163 mg, 0.55 mmol) are dissolved in 2 ml dry methylenehloride. Triethylamine (93 μl, 0.66 mmol) is added and the reaction mixture is stirred at room temperature. After complete formation of the product, the reaction mixture is quenched with water and the product is extracted with methylenehloride. The solvent is removed under reduced pressure and the crude product is absorbed to Isolute. The product is purified by automated reversed phase column chromatography (column: Interchrom Puriflash 15/35U C18, 70 g cartouche; solvents: water+0.1% trifluoroacetic acid and acetonitrile+0.1% trifluoroacetic acid) and is dried at the high vacuum pump, yielding the title compound as a white solid.

HPLC: $t_R$=10.24 min; MS-ES: (M+H)+=439; TLC*: $R_f$=0.63

Example 2

Pyrazolo[1,5-a]pyridine-3-carboxylic acid [2-methyl-5-(3-trifluoromethyl-phenylcarbamoyl)-phenyl]-amide The same procedure as in example 1 is used, except that 3-amino-4-methyl-N-(3-trifluoromethyl-phenyl)-benzamide

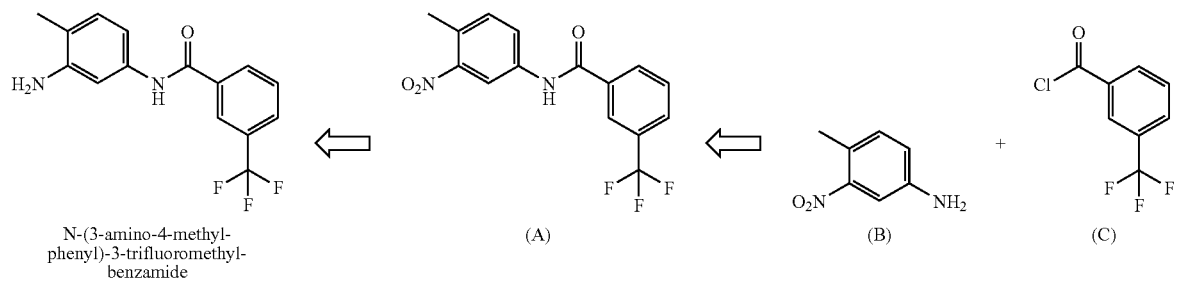

N-(3-amino-4-methyl-phenyl)-3-trifluoromethyl-benzamide          (A)          (B)          (C)

is reacted instead of N-(3-amino-4-methyl-phenyl)-3-trifluoromethyl-benzamide. The product is isolated by automated reversed phase column chromatography (column: Interchrom Puriflash 15/35U C18, 70 g cartouche; solvents: water+0.1% trifluoroacetic acid and acetonitrile+0.1% trifluoroacetic acid) and is dried at the high vacuum pump. The title compound is obtained as a white solid.

HPLC: $t_R$=10.52 min.; MS-ES: (M+H)+=439; TLC*: $R_f$=0.60

Example 3

6-Dimethylsulfamoyl-pyrazolo[1,5-a]pyridine-3-carboxylic acid [2-methyl-5-(3-trifluoromethyl-phenylcarbamoyl)-phenyl]-amide 6-Dimethylsulfamoyl-pyrazolo[1,5-a]pyridine-3-carbonyl chloride (200 mg, 0.35 mmol) and 3-amino-4-methyl-N-(3-trifluoromethyl-phenyl)-benzamide are reacted in 2 ml dry pyridine at r.t. for 18 hrs. The solvent is removed under reduced pressure. The product is isolated by automated column chromatography and is dried at the high vacuum pump, yielding the title compound as a white solid.

HPLC: $t_R$=10.76 min; MS-ES+: (M+H)+=546; TLC**: $R_f$=0.25

The starting material is prepared as follows:

Step 3.1: 6-Dimethylsulfamoyl-pyrazolo[1,5-a]pyridine-3-carbonyl chloride

6-Dimethylsulfamoyl-pyrazolo[1,5-a]pyridine-3-carboxylic acid (200 mg, 0.57 mmol) are dissolved in 4 ml chloroform and oxalylchloride (97 µl, 1.14 mmol; Fluka) are added. The reaction is refluxed for 3 hours and then volatiles are removed under reduced pressure. The crude product is directly used in the next step.

Step 3.2: 6-Dimethylsulfamoyl-pyrazolo[1,5-a]pyridine-3-carboxylic acid

The title compound is prepared according to literature procedure: Yasumitsu Tamura, Yoshio Sumida, Yasuyoshi Miki and Masazumi Ikeda, J. Chem. Soc. Perkin 1, 1974, 406-409

Step 3.3: 6-Dimethylsulfamoyl-pyrazolo[1,5-a]pyridine-3-carboxylic acid ethyl ester Potassium carbonate and ethyl propiolate are added to a stirred suspension of 1-Amino-3-dimethylsulfamoyl-pyridinium mesitylenesulfonate in chloroform at room temperature. For more details, see literature: Yasumitsu Tamura, Yoshio Sumida, Yasuyoshi Miki and Masazumi Ikeda, J. Chem. Soc. Perkin 1, 1974, 406-409

Step 3.4: 1-Amino-3-dimethylsulfamoyl-pyridinium mesitylenesulfonate

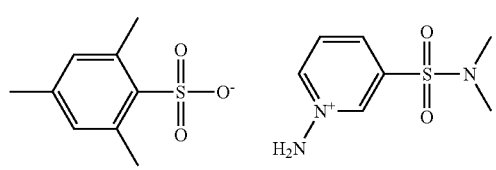

The title compound is synthesized according typical procedure using equimolar mixture of pyridine derivative and O-mesitylenesulfonylhydroxylamine (MSH), see literature Y. Tamura, J. Minamikawa, Y. Miki, S. Matsugashita and M. Ikeda, Tett. Lett. (40), 4133-4135, 1972.

Example 4

6-Dimethylsulfamoyl-pyrazolo[1,5-a]pyridine-3-carboxylic acid [5-(4-methoxy-3-trifluoromethyl-phenylcarbamoyl)-2-methyl-phenyl]-amide The same procedure as described in example 3 is used, except that 3-amino-N-(4-methoxy-3-trifluoromethyl-phenyl)-4-methyl-benzamide is used instead of 3-amino-4-methyl-N-(3-trifluoromethyl-phenyl)-benzamide. The product is isolated by automated column chromatography and is dried at the high vacuum pump, yielding the title compound as a white solid.

HPLC: $t_R$=10.26 min; MS-ES+: (M+H)+=576; TLC**: $R_f$=0.19

Example 5

6-Phenyl-pyrazolo[1,5-a]pyridine-3-carboxylic acid [2-methyl-5-(3-trifluoromethyl-phenylcarbamoyl)-phenyl]-amide The same procedure as described in example 3 steps 3.4 to 3.1 is used, except that in step 3.4 3-phenylpyridine (Fluka) is used. The product is isolated by automated column chromatography and is dried at the high vacuum pump, yielding the title compound as a white solid.

HPLC: $t_R$=11.99 min; MS-ES+: (M+H)+=515; TLC**: $R_f$=0.45

Example 6

6-Phenyl-pyrazolo[1,5-a]pyridine-3-carboxylic acid [2-methyl-5-(3-trifluoromethyl-benzoylamino)-phenyl]-amide The same procedure as described in example 3 steps 3.4 to 3.1 is used, except that in step 3.4 3-phenylpyridine (Fluka) and N-(3-amino-4-methyl-phenyl)-3-trifluoromethyl-benzamide instead of 3-amino-4-methyl-N-(3-trifluoromethyl-phenyl)-benzamide is used. The product is isolated by automated column chromatography and is dried at the high vacuum pump, yielding the title compound as a white solid.

HPLC: $t_R$=11.48 min; MS-ES+: (M+H)+=515; TLC**: $R_f$=0.26

Example 7

6-(4-Methoxy-phenyl)-pyrazolo[1,5-a]pyridine-3-carboxylic acid o-tolylamide

6-Bromo-pyrazolo[1,5-a]pyridine-3-carboxylic acid o-tolylamide (50 mg, 0.15 mmol), 4-methoxyphenylboronic acid (27.9 mg, 0.18 mmol), chloro-[2'-(dimethylamino)-2-biphenylyl]-(dinorbornylphosphine)-palladium (4.6 mg, 7.6 µmol; Fluka, CAS # 359803-53-5) and potassium carbonate (84 mg, 0.61 mmol) are heated in 5 ml dry dioxane to 130° C. for 20 minutes in the microwave oven. The product is isolated by automated column chromatography and is dried at the high vacuum pump, yielding the title compound as a white solid.

HPLC: $t_R$=11.20 min; MS-ES+: (M+H)+=358; TLC**: $R_f$=0.51

The starting material is prepared as follows:

Example 7.1

6-Bromo-pyrazolo[1,5-a]pyridine-3-carboxylic acid o-tolylamide

The same procedure as described in example 3 steps 3.4 to 3.1 is used, except that in step 3.4 3-bromopyridine (Fluka) and o-tolylamine (Fluka) instead of 3-amino-4-methyl-N-(3-trifluoromethyl-phenyl)-benzamide is used. The product is isolated by automated column chromatography and is dried at the high vacuum pump, yielding the title compound as a white solid.

HPLC: $t_R$=10.15 min; MS-ES+: (M+H)+=331; TLC***: $R_f$=0.32

Example 8

4-[4-(3-o-Tolylcarbamoyl-pyrazolo[1,5-a]pyridin-6-yl)-phenyl]-piperazine-1-carboxylic acid tert-butyl ester The same procedure as described in example 7 is used, except that 4-[4-(4,4,5,5-tetramethyl-[1,3,2]dioxaborolan-2-yl)-phenyl]-piperazine-1-carboxylic acid tert-butyl ester (Maybridge) instead of 4-methoxyphenylboronic acid is used. The product is isolated by automated column chromatography and is dried at the high vacuum pump, yielding the title compound as a white solid.

HPLC: $t_R$=11.52 min; MS-ES+: (M+H)+=512; TLC**: $R_f$=0.46

Example 9

6-(4-Morpholin-4-yl-phenyl)-pyrazolo[1,5-a]pyridine-3-carboxylic acid o-tolylamide The same procedure as described in example 7 is used, except that 4-(morpholino)phenylboronic acid (Maybridge) instead of 4-methoxyphenylboronic acid is used. The product is isolated by automated column chromatography and is dried at the high vacuum pump, yielding the title compound as a white solid.

HPLC: $t_R$=9.92 min; MS-ES+: (M+H)+=413; TLC**: $R_f$=0.30

Example 10

6-(3-Methoxy-phenyl)-pyrazolo[1,5-a]pyridine-3-carboxylic acid o-tolylamide

The same procedure as described in example 7 is used, except that 3-methoxyphenylboronic acid (Aldrich) instead of 4-methoxyphenylboronic acid is used. The product is isolated by automated column chromatography and is dried at the high vacuum pump, yielding the title compound as a white solid.

HPLC: $t_R$=10.82 min; MS-ES+: (M+H)+=358; TLC**: $R_f$=0.65

Example 11

6-(4-Dimethylamino-phenyl)-pyrazolo[1,5-a]pyridine-3-carboxylic acid o-tolylamide The same procedure as described in example 7 is used, except that 4-(dimethylamino)-phenylboronic acid (Aldrich) instead of 4-methoxyphenylboronic acid is used. The product is isolated by automated column chromatography and is dried at the high vacuum pump, yielding the title compound as a white solid.

HPLC: $t_R$=8.60 min; MS-ES+: (M+H)+=371; TLC**: $R_f$=0.57

Example 12

6-(3,4-Dimethoxy-phenyl)-pyrazolo[1,5-a]pyridine-3-carboxylic acid o-tolylamide

The same procedure as described in example 7 is used, except that 3,4-dimethoxyphenylboronic acid (Frontier) instead of 4-methoxyphenylboronic acid is used. The product is isolated by automated column chromatography and is dried at the high vacuum pump, yielding the title compound as a white solid.

HPLC: $t_R$=10.22 min; MS-ES+: (M+H)+=388; TLC**: $R_f$=0.47

Example 13

Soft Capsules 5000 soft gelatin capsules, each comprising as active ingredient 0.05 g of any one of the compounds of formula I mentioned in any one of the preceding Examples, are prepared as follows:

| Composition: | Active ingredient | 250 g |
|---|---|---|
| | Lauroglykol | 2 liters |

Preparation process: The pulverized active ingredient is suspended in Lauroglykol* (propylene glycol laurate, Gattefossé S. A., Saint Priest, France) and ground in a wet pulverizer to produce a particle size of about 1 to 3 μm. 0.419 g portions of the mixture are then introduced into soft gelatin capsules using a capsule-filling machine.

Example 14

Tablets Comprising Compounds of the Formula I

Tablets, comprising, as active ingredient, 100 mg of any one of the compounds of formula I in any one of the preceding Examples are prepared with the following composition, following standard procedures:

| Composition | |
|---|---|
| Active Ingredient | 100 mg |
| crystalline lactose | 240 mg |
| Avicel | 80 mg |
| PVPPXL | 20 mg |
| Aerosil | 2 mg |
| magnesium stearate | 5 mg |
| | 447 mg |

Manufacture: The active ingredient is mixed with the carrier materials and compressed by means of a tabletting machine (Korsch EKO, stamp diameter 10 mm).

Avicel® is microcrystalline cellulose (FMC, Philadelphia, USA). PVPPXL is polyvinyl-polypyrrolidone, cross-linked (BASF, Germany). Aerosil® is silicon dioxide (Degussa, Germany).

Example 15

Inhibition of EphB4 Kinase Activity

Using the test system described above in the general description, the compounds of Examples 1 and 2 are tested for their ability to inhibit EphB4 kinase. $IC_{50}$ values (µmol/l) especially in the range given in the general description are found.

The invention claimed is:
1. A compound of the formula

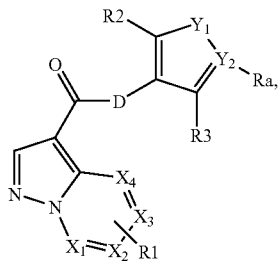

(I)

wherein

R1 is hydrogen, halo, sulfamoyl, N—$C_{1-4}$alkyl sulfamoyl, N,N-di-$C_{1-4}$alkyl sulfamoyl, unsubstituted or substituted alkyl, unsubstituted or substituted aryl, unsubstituted or substituted cycloalkyl or unsubstituted or substituted heterocyclyl;

each of R2 and R3 is, independency of the other, hydrogen, halo, $C_{1-4}$-alkyl, trifluoromethyl, $C_{1-4}$-alkoxy or cyano, $X_1$, $X_2$, $X_3$ and $X_4$ are CH;

D is N(R6), O or S,
  wherein R6 is hydrogen, acyl or unsubstituted or substituted alkyl, $Y_1$ is O, S, NH, $CH_2$, N=CH, CH=N or CH=CH;
$Y_2$ is C or, if Ra is absent, can be N;
Ra is
  absent if $Y_2$ is N and R1 is unsubstituted alkyl with 5 or more carbon atoms, substituted alkyl, unsubstituted or substituted aryl, unsubstituted or substituted cycloalkyl or unsubstituted or substituted heterocyclyl, or,
  if $Y_2$ is C, is hydrogen if R1 is unsubstituted alkyl with 5 or more carbon atoms, substituted alkyl, unsubstituted or substituted aryl, unsubstituted or substituted cycloalkyl or unsubstituted or substituted heterocyclyl,
  or, if $Y_2$ is C and R1 is hydrogen, halo, $C_{1-4}$-alkyl, sulfamoyl, N—$C_{1-4}$alkyl sulfamoyl, N,N-di-$C_{1-4}$alkyl sulfamoyl, or unsubstituted aryl, is a moiety of the formula

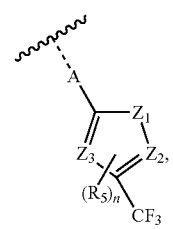

(IA)

wherein the dotted line means the bond binding to the rest of the molecule of the formula I (which is indicated by the wave line),
A is C(=O)—N(R4) or N(R4)-C(=O),
  wherein R4 is hydrogen or unsubstituted or substituted alkyl,
$Z_1$ is O, S, NH, $CH_2$, CH=N, N=CH or CH=CH,
$Z_2$ is nitrogen or CH,
$Z_3$ is CH or N,
each $R_5$ present is, independency of the others, a substituent and
n is 0, 1 or 2,
in free form or in salt form.

2. The compound according to claim 1 of the formula I, wherein

R1 is hydrogen, halo, $C_1$-$C_{20}$-alkyl that is unsubstituted or substituted by one or more substituents independently selected from the group consisting of unsubstituted or substituted heterocyclyl as described below, unsubstituted or substituted cycloalkyl as described below, unsubstituted or substituted aryl as defined below, especially phenyl or naphthyl; of $C_2$-$C_7$-alkenyl, $C_2$-$C_7$-alkynyl, halo, hydroxy, $C_1$-$C_7$-alkoxy, $C_1$-$C_7$-alkoxy-$C_1$-$C_7$-alkoxy, ($C_1$-$C_7$-alkoxy)-$C_1$-$C_7$-alkoxy-$C_1$-$C_7$-alkoxy, phenoxy, naphthyloxy, phenyl- or naphthyl-$C_1$-$C_7$-alkoxy; amino-$C_1$-$C_7$-alkoxy, $C_1$-$C_7$-alkanoyloxy, benzoyloxy, naphthoyloxy, nitro, cyano, carboxy, $C_1$-$C_7$-alkoxy carbonyl, phenyl- or naphthyl-$C_1$-$C_7$-alkoxycarbonyl, $C_1$-$C_7$-alkanoyl, benzoyl, naphthoyl, carbamoyl, N-mono- or N,N-di-substituted carbamoyl wherein the substitutents are selected from $C_1$-$C_7$-alkyl and hydroxy-$C_1$-$C_7$-alkyl; amidino, guanidino, ureido, mercapto, $C_1$-$C_7$-alkylthio, phenyl- or naphthylthio, phenyl- or naphthyl-$C_1$-$C_7$-alkylthio, $C_1$-$C_7$-alkyl-phenylthio, $C_1$-$C_7$-alkyl-naphthylthio, halogen-$C_1$-$C_7$-alkylmercapto, $C_1$-$C_7$-alkylsulfinyl, phenyl- or naphthyl-sulfinyl, phenyl- or naphthyl-$C_1$-$C_7$-alkylsulfinyl, $C_1$-$C_7$-alkyl-phenylsulfinyl, $C_1$-$C_7$-alkyl-napthylsulfinyl, sulfo, $C_1$-$C_7$-alkanesulfonyl, phenyl- or naphthyl-sulfonyl, phenyl- or naphthyl-$C_1$-$C_7$-alkylsufonyl, $C_1$-$C_7$-alkylphenylsulfonyl, halogen-$C_1$-$C_7$-alkylsulfonyl, sulfonamido, benzosulfonamido, amino, N-mono- or N,N-di-[$C_1$-$C_7$- alkyl, phenyl and/or phenyl-$C_1$-$C_7$-alkyl)-amino; where each phenyl or naphthyl, also in phenoxy or naphthoxy, mentioned above as substituent or part of a substituent of substituted alkyl is itself unsubstituted or substituted by one or more, e.g. up to three, preferably 1 or 2, substituents independency selected from halo, halo-$C_1$-$C_7$-alkyl, hydroxy, $C_1$-$C_7$-alkoxy, amino, N-mono- or N,N-di-($C_1$-$C_7$-alkyl, phenyl, naphthyl, phenyl-$C_1$-$C_7$-alkyl and/or naphthyl-$C_1$-$C_7$-alkyl)-amino, nitro, carboxy, $C_1$-$C_7$-alkoxycarbonyl carbamoyl, cyano and/or sulfamoyl; unsubstituted or substituted aryl which is an unsaturated carbocyclic system of not more than 20 carbon atoms, especially not more than 16 carbon atoms, and is mono-, bi- or tricyclic, which is unsubstituted or, in the case of substituted aryl, substituted by one or more, preferably up to three, e.g. one or two substituents independently selected from the group consisting of phenyl naphthyl, phenyl- or naphthyl-$C_1$-$C_7$-alkyl, hydroxy-$C_1$-$C_7$-alkyl, $C_1$-$C_7$-alkoxy-$C_1$-$C_7$-alkyl, ($C_1$-$C_7$-alkoxy)-$C_1$-$C_7$alkoxy-$C_1$-$C_7$-alkyl, $C_1$-$C_7$-alkanoyl-$C_1$-$C_7$-alkyl, halo-$C_1$-$C_7$-alkyl, such as trifluoromethyl; phenoxy- or naphtyloxy-$C_1$-$C_7$-alkyl, phenyl- or naphthyl-$C_1$-$C_7$-alkoxy-$C_1$-$C_7$-alkyl, $C_1$-$C_7$-alkoxy-carbonyloxy-$C_1$-$C_7$-alkyl, phenyl- or naphthyl-$C_1$-$C_7$-alkoxycarbonyloxy-$C_1$-$C_7$-alkyl, cyano-$C_1$-$C_7$-alkyl, $C_2$-$C_7$-alkenyl, $C_2$-$C_7$-alkynyl, $C_1$-$C_7$-alkanoyl, halo, hydroxy, $C_1$-$C_7$-alkoxy, $C_1$-$C_7$-alkoxy-$C_1$-$C_7$-alkoxy, ($C_1$-$C_7$-alkoxy)-$C_1$-$C_7$-alkoxy-$C_1$-$C_7$-alkoxy, phenoxy, naphthyloxy, phenyl- or naphthyl-$C_1$-$C_7$-alkoxy, amino-$C_1$-$C_7$-alkoxy, $C_1$-$C_7$-alkanoyloxy, benzoyloxy, naphthoyloxy, nitro, amino, mono-, di or tri-substituted amino wherein the amino substituents are independently selected from $C_1$-$C_7$-alkyl, $C_1$-$C_7$-alkanoyl, $C_1$-$C_7$-alkanesulfonyl, phenyl, naphthyl, phenyl-$C_1$-$C_7$-alkyl and naphthyl-$C_1$-$C_7$-alkyl; cyano, carboxy, $C_1$-$C_7$-alkoxy carbonyl, phenyl- or naphthyl-$C_1$-$C_7$-alkoxycarbonyl, benzoyl, naphthoyl, carbamoyl, N-mono- or N,N-disubstituted carbamoyl wherein the substitutents are selected from $C_1$-$C_7$-alkyl and hydroxy-$C_1$-$C_7$-alkyl; amidino, guanidino, ureido, mercapto, $C_1$-$C_7$-alkylthio, phenyl- or naphthylthio, phenyl- or naphthyl-$C_1$-$C_7$-alkylthio, $C_1$-$C_7$-alkyl-phenylthio, $C_1$-$C_7$-alkyl-naphthylthio, halogen-$C_1$-$C_7$-alkylmercapto, $C_1$-$C_7$-alkylsulfinyl, phenyl- or naphthyl-sulfinyl, phenyl- or naphthyl-$C_1$-$C_7$-alkylsulfinyl, $C_1$-$C_7$-alkyl-phenylsulfinyl, $C_1$-$C_7$-alkyl-napthylsulfinyl, sulfo, $C_1$-$C_7$-alkanesulfonyl, phenyl- or naphthyl-sulfonyl, phenyl- or naphthyl-$C_1$-$C_7$-alkylsulfonyl, $C_1$-$C_7$-alkylphenylsulfonyl, halogen-$C_1$-$C_7$-alkylsulfonyl, sulfonamido, benzosulfonamido, pyrrolidino, piperidino, piperidino substituted by amino or N-mono- or N,N-di-[$C_1$-$C_7$-alkyl, phenyl and/or phenyl-$C_1$-$C_7$-alkylyamino, unsubstituted or N—$C_1$-$C_7$-alkyl substituted piperidinyl bound via a ring carbon atom, piperazino, $C_1$-$C_7$-alkylpiperazino, morpholino or thiomorpholino; where each phenyl or naphthyl mentioned above as substitutent or part of a substituent of substituted aryl is itself unsubstituted or substituted by one or more substituents independently selected from halo, halo-$C_1$-$C_7$-alkyl, hydroxy, $C_1$-$C_7$-alkoxy, amino, N-mono- or N,N-di-($C_1$-$C_7$-alkyl, phenyl, naphthyl, phenyl-$C_1$-$C_7$-alkyl and/or naphthyl-$C_1$-$C_7$-alkyl) amino, nitro, carboxy, $C_1$-$C_7$-alkoxycarbonyl, carbamoyl, cyano and/or sulfamoyl;

unsubstituted or substituted cycloalkyl wherein cycloalkyl is a saturated mono- or bicyclic hydrocarbon group with 3 to 16 ring carbon atoms and is substituted by one or more substitutents independently selected from those described for substituted aryl or is unsubstituted; or unsubstituted or substituted heterocyclyl wherein heterocyclyl is a heterocyclic radical that is unsaturated, saturated or partially saturated and is a monocyclic or bicyclic or tricyclic ring; and has 3 to 24; wherein one or more carbon ring atoms are replaced by a heteroatom selected from the group consisting of nitrogen, oxygen and sulfur, the bonding ring having 4 to 12 ring atoms; which heterocyclic radical is unsubstituted or substituted by one or more substituents independently selected from the group consisting of the substituents defined above under "substituted aryl"; and where heterocyclyl is especially a heterocyclyl radical selected from the group consisting of oxiranyl, azirinyl, aziridinyl, 1,2-oxathiolanyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, (S-oxo or S,S-dioxo)-thiomorpholinyl, indolizinyl, isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, beta-carbolinyl, phenanthridinyl, acridinyl, perimidinyl, phenanthrolinyl, furazanyl, phenazinyl, phenothiazinyl, phenoxazinyl, chromenyl, isochromanyl and chromanyl, each of these radicals being unsubstituted or substituted by one to three of the substituents mentioned as substitutents for substituted aryl;

each of R2 and R3 is, independently of the other, hydrogen, halo, $C_1$-$C_4$-alkyl, trifluoromethyl, $C_1$-$C_4$-alkoxy or cyano, $X_1$, $X_2$, $X_3$ and $X_4$ are CH;

D is N(R6), O or S, wherein R6 is hydrogen, $C_1$-$C_7$-alkanoyl, benzoyl, naphthoyl, phenyl-$C_1$-$C_7$-alkanoyl, naphthyl-$C_1$-$C_7$alkanoyl, phenylsulfonyl or lower alkanesulfonyl, or unsubstituted or substituted alkyl;

$Y_1$ is O, S, NH, $CH_2$, N=CH, CH=N or CH=CH;

$Y_2$ is C or, if Ra is absent, can be N;

Ra is absent if $Y_2$ is N and R1 is $C_5$-$C_{20}$-alkyl, substituted alkyl as defined above, unsubstituted or substituted aryl as defined above, unsubstituted or substituted cycloalkyl as defined above or unsubstituted or substituted heterocyclyl as defined above, or, if $Y_2$ is C, is hydrogen if R1 is $C_5$-$C_{20}$-alkyl, substituted alkyl as defined above, unsubstituted or substituted aryl as defined above, unsubstituted or substituted cycloalkyl as defined above or unsubstituted or substituted heterocyclyl as defined above, or, if $Y_2$ is C and R1 is hydrogen, halo or $C_1$-$C_4$-alkyl, is a moiety of the formula

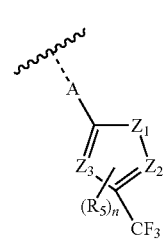

(IA)

wherein the dotted line means the bond binding to the rest of the molecule of the formula I, A is C(=O)—N(R4) or N(R4)-C(=O), wherein R4 is hydrogen or unsubstituted or substituted alkyl as defined above, $Z_1$ is O, S, NH, $CH_2$, CH=N, N=CH or CH=CH,
$Z_2$ is nitrogen or CH,
$Z_3$ is CH or N,
each R5 present is, independently of the others, a substituent selected from the group consisting of $C_1$-$C_7$-alkyl, halo, halo-$C_1$-$C_7$-alkyl, $C_1$-$C_7$-alkanoyl, hydroxy, $C_1$-$C_7$-alkoxy, nitro, amino, mono- or disubstituted amino wherein the amino substituents are independently selected from $C_1$-$C_7$-alkyl and $C_1$-$C_7$-alkanoyl, cyano, carboxy, $C_1$-$C_7$-alkoxy carbonyl, carbamoyl, N-mono- or N,N-di-($C_1$-$C_7$-alkyl)-substituted carbamoyl, amidino, guanidino, ureido, lower alkylthio, sulfo, $C_1$-$C_7$-alkanesulfonyl and sulfonamido; and
n is 0, 1 or 2.

3. A The compound according to claim 1 of the formula I, wherein
R1 is hydrogen, halo or $C_1$-$C_4$-alkyl;
each of R2 and R3 is, independently of the other, hydrogen, $C_1$-$C_4$-alkyl, halo or cyano;
each of $X_1$, $X_2$, $X_3$ and $X_4$ is CH;
D is N(R6) wherein R6 is hydrogen, $C_1$-$C_7$-alkanoyl, $C_1$-$C_7$-alkyl or phenyl-$C_1$-$C_7$-alkyl;
$Y_1$ is CH=CH;
$Y_2$ is C;
Ra is a moiety of the formula

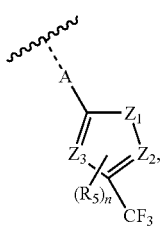

(IA)

wherein the dotted line means the bond binding to the rest of the molecule of the formula I,
A is C(=O)—N(R4) or N(R4)-C(=O),
wherein R4 is hydrogen or $C_1$-$C_7$-alkyl,
$Z_1$ is CH=CH,
$Z_2$ is N or CH,
$Z_3$ is CH,
each $R_5$ present is, independently of the others, a substituent selected from the group consisting of $C_1$-$C_7$-alkyl, halo-$C_1$-$C_7$-alkyl, $C_1$-$C_7$alkanoyl, hydroxy, $C_1$-$C_7$alkoxy, amino, mono- or di-substituted amino wherein the amino substituents are independently selected from $C_1$-$C_7$alkyl and $C_1$-$C_7$-alkanoyl, cyano, carboxy, $C_1$-$C_7$-alkoxy carbonyl, carbamoyl and N-mono- or N,N-di-($C_1$-$C_7$-alkyl)-substituted carbamoyl, and
n is 0, 1 or 2.

4. A The compound according to claim 1 of the formula I, selected from the group of compounds consisting of
pyrazolo[1,5-a]pyridine-3-carboxylic acid [2-methyl-5-(3-trifluoromethyl-benzoylamino)-phenyl]-amide,
pyrazolo[1,5-a]pyridine-3-carboxylic acid [2-methyl-5-(3-trifluoromethyl-phenylcarbamoyl)-phenyl]-amide,
6-Dimethylsulfamoyl-pyrazolo[1,5-a]pyridine-3-carboxylic acid [2-methyl-5-(3-trifluoromethyl-phenylcarbamoyl)-phenyl]-amide,
6-Dimethylsulfamoyl-pyrazolo[1,5-a]pyridine-3-carboxylic acid [5-(4-methoxy-3-trifluoromethyl-phenylcarbamoyl)-2-methyl-phenyl]-amide,
6-Phenyl-pyrazolo[1,5-a]pyridine-3-carboxylic acid [2-methyl-5-(3-trifluoromethyl-phenylcarbamoyl)-phenyl]-amide,
6-Phenyl-pyrazolo[1,5-a]pyridine-3-carboxylic acid [2-methyl-5-(3-trifluoromethyl-benzoylamino)-phenyl]-amide,
6-(4-Methoxy-phenyl)-pyrazolo[1,5-a]pyridine-3-carboxylic acid o-tolylamide,
4-[4-(3-o-Tolylcarbamoyl-pyrazolo[1,5-a]pyridin-6-yl)-phenyl]-piperazine-1-carboxylic acid tert-butyl ester,
6-(4-Morpholin-4-yl-phenyl)-pyrazolo[1,5-a]pyridine-3-carboxylic acid o-tolylamide,
6-(3-Methoxy-phenyl)-pyrazolo[1,5-a]pyridine-3-carboxylic acid o-tolylamide,
6-(4-Dimethylamino-phenyl)-pyrazolo[1,5-a]pyridine-3-carboxylic acid o-tolylamide and
6-(3,4-Dimethoxy-phenyl)-pyrazolo[1,5-a]pyridine-3-carboxylic acid o-tolylamide,
in each case in free form or in salt form.

5. A pharmaceutical preparation, comprising:
the compound as defined in claim 1 of the formula I, in free form or in pharmaceutically acceptable salt form, and a pharmaceutically acceptable carrier.

6. A process for the manufacture of a compound as defined in claim 1 of the formula I, in free form or in salt form, comprising
a) condensing a carbonic acid of the formula

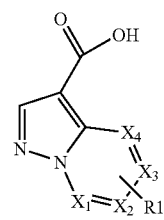

(II)

or a reactive derivative thereof, wherein R1, $X_1$, $X_2$, $X_3$ and $X_4$ are as defined for a compound of the formula I, with a compound of the formula

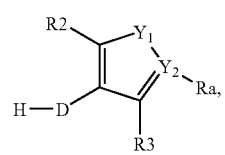

(III)

wherein R2, R3, D, $Y_1$, $Y_2$ and Ra are as defined for a compound of the formula I or
b) for the synthesis of a compound of the formula I, wherein R1 is unsubstituted or substituted alkyl, unsubstituted or substituted aryl, unsubstituted or substituted cycloalkyl or unsubstituted or substituted heterocyclyl, reacting a boronic acid of the formula

R1-B(A)$_2$ (IV), wherein R1 is unsubstituted or substituted alkyl, unsubstituted or substituted aryl (preferred), unsubstituted or substituted cycloalkyl or unsubstituted or substituted heterocyclyl (each bound via a C-Atom) and A is hydroxy or lower alkoxy or $B(A)_2$ is 9-borabicyclo[3.3.1]nonanyl or $-B(CHCH_3CH(CH_3)_2)_2$, with a compound of the formula

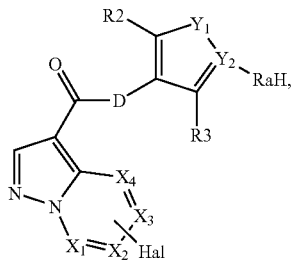

(V)

wherein R1, R2, R3, $X_1$, $X_2$, $X_3$, $X_4$, $Y_1$, $Y_2$, D and Ra are as defined for a compound of the formula I and Hal is halo, especially chloro, iodo or preferably bromo, or (perfluorinated $C_1$-$C_4$-alkyl)-sulfonyloxy;

and, if desired, transforming a compound of the formula I into a different compound of the formula I, transforming a salt of an obtainable compound of the formula I into the free compound or a different salt, transforming an obtainable free compound of the formula I into a salt thereof, and/or separating an obtainable mixture of isomers of a compound of the formula I into individual isomers.

* * * * *